(12) United States Patent
Yamashita et al.

(10) Patent No.: US 9,285,368 B2
(45) Date of Patent: Mar. 15, 2016

(54) METHOD FOR ANALYZING PSA, AND A METHOD FOR DISTINGUISHING PROSTATE CANCER FROM PROSTATIC HYPERTROPHY USING THAT METHOD FOR ANALYZING PSA

(75) Inventors: Katsuko Yamashita, Yokohama (JP); Keiko Fukushima, Yokohama (JP)

(73) Assignees: TOKYO INSTITUTE OF TECHNOLOGY, Tokyo (JP); KONICA MINOLTA HOLDINGS, INC., Tokyo (JP)

( * ) Notice: Subject to any disclaimer, the term of this patent is extended or adjusted under 35 U.S.C. 154(b) by 878 days.

(21) Appl. No.: 13/505,280

(22) PCT Filed: Mar. 4, 2010

(86) PCT No.: PCT/JP2010/054062
§ 371 (c)(1),
(2), (4) Date: Jul. 23, 2012

(87) PCT Pub. No.: WO2011/052244
PCT Pub. Date: May 5, 2011

(65) Prior Publication Data
US 2012/0282612 A1  Nov. 8, 2012

(30) Foreign Application Priority Data

Oct. 30, 2009  (JP) ................................ 2009-250066

(51) Int. Cl.
*G01N 33/573*  (2006.01)
*G01N 33/574*  (2006.01)

(52) U.S. Cl.
CPC ........ *G01N 33/573* (2013.01); *G01N 33/57434* (2013.01); *G01N 2333/4724* (2013.01); *G01N 2333/91102* (2013.01); *G01N 2333/96433* (2013.01)

(58) Field of Classification Search
None
See application file for complete search history.

(56) References Cited

U.S. PATENT DOCUMENTS

| 2004/0147033 | A1 | 7/2004 | Shriver et al. |
| 2009/0023220 | A1 | 1/2009 | Amano et al. |
| 2011/0236995 | A1 | 9/2011 | Hirano et al. |
| 2011/0294141 | A1 | 12/2011 | Yamashita et al. |

FOREIGN PATENT DOCUMENTS

| CN | 101213454 A | 7/2008 |
| GB | 2 361 060 A | 10/2001 |
| GB | 2 379 444 A | 3/2003 |
| JP | 2002-055108 A | 2/2002 |
| JP | 2006-515927 A | 6/2006 |
| WO | 2004/066808 A2 | 8/2004 |
| WO | 2006/125580 A1 | 11/2006 |

OTHER PUBLICATIONS

Fukushima et al., "Carbohydrate structural changes of prostate specific antigen between prostate cancer and benign prostate hypertrophy," 29th Japan Society for Molecular Tumor Marker Research Program Compendium, 2009, pp. 84-85.
Fukushima et al., "alpha1,2-Fucosylated and beta-N-acetylgalactosaminylated prostate-specific antigen as an efficient marker of prostatic cancer," Glycobiology, 2010, vol. 20(4), pp. 452-460.
Gotoh et al., "Molecular cloning and characterization of beta1,4-N-acetylgalactosaminyltransferases IV synthesizing N,N'-diacetyl-lactosediamine," FEBS Letters, 2004, vol. 562(1-3), pp. 134-140.
Mollicone et al., "Molecular genetics of alpha-L-fucosyltransferase genes (H, Se, Le, FUT4, FUT5 and FUT6)," Transfus. Clin. Biol., 1994, vol. 1(2), pp. 91-97.
Ohyama et al., "Carbohydrate structure and differential binding of prostate specific antigen to *Maackia amurensis* lectin between prostate cancer and benign prostate hypertrophy," Glycobiology, 2004, vol. 14, pp. 671-679.
Peracaula et al., "Altered glycosylation pattern allows the distinction between prostate-specific antigen (PSA) from normal and tumor origins," Glycobiology, 2003, vol. 13(6), pp. 457-470.
Tajiri et al., "Oligosaccharide profiles of the prostate specific antigen in free and complexed forms from the prostate cancer patient serum and in seminal plasma: a glycopeptide approach," Glycobiology, 2008, vol. 18, pp. 2-8.
International Search Report, date of mailing Apr. 20, 2010, PCT Application No. PCT/JP2010/054062, 2 pages.
Arenas et al., "A lectin histochemistry comparative study in human normal prostate, benign prostatic hyperplasia, and prostatic carcinoma," Glycoconjugate Journal, vol. 16, No. 7, Jul. 1, 1999, pp. 375-382.
Fukushima et al., (Nov. 1998) "Elevated Serum Levels of *Trichosanthese japonica* Agglutinin-I Binding Alkaline Phosphatase in Relation to High-Risk Groups for Hepatocellular Carcinomas," Clin. Cancer Res., pp. 2771-2777; vol. 4.
Fukushima et al., (Oct. 1998) "Elevation of $\alpha 2 \rightarrow 6$ Sialytransferase and $\alpha 1 \rightarrow 2$ Fucosyltransferase Activities in Human Choriocarcinoma," Cancer Research, vol. 58, pp. 4301-4306.
Guang et al., "Structural alterations and significance of sugar chains of PSA in urine and blood from BPH and PCa patients," Chinese Journal of Andrology, 2008, vol. 22, No. 6, pp. 33-35.
Invitrogen Catalog, Lectin SBA Conjugates, Dec. 15, 2006, pp. 1-3.
McMahon et al., "Evaluation of three techniques for differential diagnosis of prostatic needle biopsy specimens," Journal of Clinical Pathology, BMJ Publishing Group, GB, vol. 45, No. 12, Jan. 1, 1992, pp. 1094-1098.

(Continued)

*Primary Examiner* — Anand Desai
(74) *Attorney, Agent, or Firm* — Kilpatrick Townsend & Stockton LLP

(57) ABSTRACT

A method for distinguishing prostate cancer from prostatic hypertrophy using the method for analyzing PSA and an analysis kit of PSA are provided.
An object of the present invention can be solved by being brought into contact a lectin having an affinity for β-N-acetyl-galactosamine residues with a sample possibly containing PSA, to determine an amount of PSA having an affinity for the lectin. A method for distinguishing prostate cancer from prostatic hypertrophy can be provided by this method.

7 Claims, 4 Drawing Sheets

(56) References Cited

OTHER PUBLICATIONS

Oyama, "Zenritsusen Gan Screening no Atarashii Tenkai Gan Tokuiteki PS Awa Sonzai Suruka?: PSA no Tosa Kozo Kaiseki kara," Urology View; 2005; 77-82; vol. 3, No. 4.

Tabares et al., "Different glycan structures in prostate-specific antigen from prostate cancer sera in relation to seminal plasma PSA," Glycobiology; 2006; 132-145; vol. 16, No. 2.

Yamashita et al., (1992) "Purification and Characterization of a Fucα1→2Galβ1→and GalNAcβ1→specific Lectin in Root Tubers of Trichosanthese japonica," J. Biol. Chem., 25414-25422; vol. 267, No. 35.

Yamashita et al., (1995) "Expression of Siaα2→6Galβ1→4GlcNAc Residues on Sugar Chains of Glycoproteins Including Carcinoembryonic Antigens in Human Colon Adenocarcinoma: Applications of Trichosanthes japonica Agglutinin I for Early Diagnosis," Cancer Res, 1675-1679; vol. 55.

BPH serum PSA

PC serum PSA

METHOD FOR ANALYZING PSA, AND A METHOD FOR DISTINGUISHING PROSTATE CANCER FROM PROSTATIC HYPERTROPHY USING THAT METHOD FOR ANALYZING PSA

CROSS-REFERENCE TO RELATED APPLICATIONS

The present application is a 371 National Phase application of PCT/JP2010/054062, filed Mar. 4, 2010, which application claims priority to JP 2009-250066, filed Oct. 30, 2009.

TECHNICAL FIELD

The present invention relates to a method for analyzing PSA (Prostate Specific Antigen), and a method for distinguishing prostate cancer from prostatic hypertrophy using that method for analyzing PSA, and an analysis kit for PSA. According to the present invention, prostate cancer and prostatic hypertrophy can be clearly distinguished by using a lectin which binds to the carbohydrate chain specifically expressed in PSA secreted by cancer cells of the prostate cancer. Particularly, prostate cancer and prostatic hypertrophy can be clearly distinguished by using the lectin, which binds to the carbohydrate chain specifically expressed in PSA secreted by cancer cells of the prostate cancer, and sialidases.

Further, the present invention relates to a method for detecting the prostate cancer, characterized in that expression of fucosyltransferase 1 or β-N-acetylgalactosaminyltransferase 4 in a sample derived from the living body is analyzed. According to the present invention, prostate cancer patients and normal men or prostatic hypertrophy patients can be distinguished.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 28313-19.TXT, created on Jul. 12, 2012, 16,384 bytes, machine format IBM-PC, MS-Windows operating system, is hereby incorporated by reference in its entirety for all purposes.

BACKGROUND ART

Prostate cancer is mainly developed in men 60 years or older. The prostatic cancer has become the second leading cause of cancer-related death, after lung cancer, for men in the American and European countries. The incidence of prostate cancer has increased since 1975, and one of the reasons is the spread of diagnosis using the measurement of the prostate specific antigen (hereinafter referred to as PSA). Early cancer which is difficult to detect by a conventional digital rectal examination has been found by the measurement of PSA.

PSA is a protein secreted in a glandular cavity of the prostate from glandular cells of the prostate. PSA is expressed in the prostate tissue-specifically, but not cancer-specifically. Thus, it is known that the PSA is increased in the benign diseases such as prostatic hypertrophy and prostatitis other than the prostate cancer.

At present, the PSA assay widely used is total PSA assay wherein both complexed PSA, in which PSA bound to α1-antichymotrypsin (hereinafter sometimes referred to as PSA-ACT), and free PSA can be measured. When the measured value of total PSA of a subject is not less than 10 ng/mL, the possibility of prostate cancer is 50% or more of the subject. Twenty five percent of patients having a total PSA value of 4-10 ng/mL are prostate cancer patients, and 15% of patients having a total PSA value of 2-4 ng/mL are prostate cancer patients. The range of 4-10 ng/mL of total PSA is refered to as gray zone. Even in the case of patients having prostatic hypertrophy, there are many patients having a total PSA value of the gray zone. For this reason, the development of a method for analyzing PSA, which can distinguish between prostate cancer patients and prostatic hypertrophy patients, is desired.

Measuring the ratio of free PSA to total PSA is carried out in order to distinguish prostate cancer from prostatic hypertrophy in patients having total PSA values in the gray zone. It has been reported that the ratios of free PSA to total PSA in sera of prostate cancer patients is lower than that in normal sera. Free PSA value is measured by the ELISA method for free PSA. Then the ratio of free PSA value to total PSA value (hereinafter sometimes referred to as "free/total PSA ratio") is calculated. When the value of a free/total PSA ratio is not more than 25%, there exists tumors in the prostate at the high frequency. However, in samples of the gray zone, the probability of prostate cancer is 56% in cases having a free/total PSA ratio of 0 to 10%, the probabilty of prostate cancer is 28% in cases having a free/total PSA ratio of 10-15%, the probabilty of a prostate cancer is 20% in cases having a free/total PSA ratio of 15-20%, and the probabilty of a prostate cancer is 16% in cases having a free/total PSA ratio of 20-25%. Thus, even if a free/total PSA ratio is used, it is not easy to distinguish prostate cancer from prostatic hypertrophy.

In the case of the patients having more than 10 ng/mL of total PSA and the patients having 4-10 ng/mL (gray zone) of total PSA and not more than 25% in a free PSA/total PSA ratio, a biopsy of prostate grand is performd for a definitive diagnosis of the prostate cancer. However, in the latter patients, prostate cancer can be detected at the possibility around 30%. Therefore, patient is placed an excessive burden. For this reason, the development of a method for simply and easily distinguishing prostate cancer from prostatic hypertrophy has been desired.

It is known that PSA is a glycoprotein having one asparagine-linked carbohydrate chain (hereinafter referred to as an N-glycan chain), and the PSA from prostate cancer patients has higher-branched complex type of N-glycans. Further, it has been considered that PSA of prostate cancer patients might have a cancer-specific carbohydrate chain. For example, an N-glycan chain of PSA secreted from LNCaP cells derived from a prostate cancer was analyzed by using a mass spectrometer. As a result, it was reported that the N-glycan chain has a high content of N-acetylhexosamine (HexNAc) and fucose, and less sialic acids as compared to an N-glycan chain in PSA of normal seminal fluid (non-patent document 1). However, the sugar chain structure of PSA from the LNCaP cells is different from that in serum PSA in prostate cancer patients, because the carbohydrate chain in PSA of the LNCaP cells contains less sialic acid residues. Therefore, the charactes of PSA from LNCaP cells were not considered to be the same as those of PSA from prostate cancer patients.

Also, Oyama et al. found that N-glycans of PSA in the prostate cancer patient serum contained sialic acid α(2,3) galactose residues (Sialic acid α 2,3 Gal-R), and that more sialic acid α(2,3) galactose residues were linked to PSA of prostate cancer patient serum as compared to PSA of prostatic hypertrophy patient serum (patent Reference 1 and non-patent Reference 2). Further, a method for distinguishing prostate cancer from prostatic hypertrophy has been found by binding PSA from the prostate cancer patient serum to Maackia amurensis agglutinin (hereinafter referred to as MAA) which can specifically bind to the sialic acid α(2,3) galactose residues, and measuring the ratio of MAA-bound PSA to total PSA (patent reference 1 and non-patent reference 2). However, besides PSA, α1-antichymotrypsin has the sialic acid α(2,3) galactose residues, and therefore α1-antichymotrypsin can also bind to MAA. Thus, in the case of the PSA bound to α1-antichymotrypsin, i.e. PSA-ACT, PSA having sialic acid α(2,3) galactose residues cannot be separated from PSA lacking sialic acid α(2,3) galactose residues. Thus, it is necessary to measure free PSA in order to distinguish a prostate cancer patient from a prostatic hypertrophy patient.

Tajiri et al. have compared the sugar chain structures of PSA from two prostate cancer patient sera to that of PSA in normal seminal fluid by using mass spectrometry. It has been reported that PSA of the prostate cancer patient serum is sialylated and fucosylated (non-patent reference 3). However, it has not been reported that a prostate cancer patient can be distinguished from a prostatic hypertrophy patient by the analysis of carbohydrate chains other than the sialic acid α(2,3) galactose residues.

CITATION LIST

Patent Reference patent Literature 1: Japanese Unexamined Patent Publication (Kokai) 2002-55108

Non Patent Literature non-patent reference 1: Glycobiology, 2003, (the United state), vol. 13, p. 457-470
non-patent reference 2: Glycobiology, 2004, (the United state), vol. 14, p. 671-679
non-patent reference 3: Glycobiology, 2008, (the United state), vol. 18, p. 2-8

SUMMARY OF INVENTION

Technical Problem

The present inventors disclosed the following invention in Japanese Patent Application No. 2009-023597 (undisclosed).

The present inventors have attempted to distinguish PSA of normal men from PSA of prostate cancer patients by using a lectin-immobilized column i.e. MAA described in patent reference 1, and to measure PSA bound to MAA columns. However, when PSA was separated by using an MAA column, the recovery rate of normal PSA which does not have sialic acid α(2,3) galactose residues was 70%. Therefore, this result indicated that PSA nonspecifically bound to the MAA column. Also, the recovery rate of PSA from prostate cancer patient serum was 40%, suggesting that PSA having sialic acid α(2,3) galactose residues was not eluted with 0.4M lactose from the MAA column in addition to nonspecific binding of the MAA column. Thus, these results indicated that the amount of PSA having sialic acid α(2,3) galactose residues cannot be accurately measured when the MAA column is used.

At present, not less than 100 kinds of lectin are commercially available. The present inventors have carried out research on the determination of the carbohydrate structures expressed on PSA from prostate cancer patient serum by using combinations of various plant lectins having different carbohydrate binding abilities, and then have conducted intensive studies into a method for distinguishing between PSA of prostate cancer and PSA of prostatic hypertrophy. As a consequence, the present inventors have found that in the blood of a prostate cancer patient, there exists PSA having an affinity for *Trichosanthes japonica* agglutinin-II (hereinafter sometimes referred to as TJA-II) or *Wisteria floribunda* agglutinin (hereinafter sometimes referred to as WFA), and also the present inventors have been able to distinguish between PSA from prostate cancer patient serum and PSA from prostatic hypertrophy patient serum by using TJA-II or WFA. More particularly, the present inventors found that serum PSA from most prostate cancer patients has β-N-acetylgalactosamine residues (GalNAcβ1→R) and/or fucose α(1,2) galactose residues (Fucα1→2Galβ1→R).

The present inventors have further studied the more cancer-specific carbohydrate chain structure which expresses in the PSA from the prostate cancer patient serum. The present inventors have found that if sialic acid residues linked to the PSA of prostate cancer patient serum was removed by *Arthrobactor sialidase* which cleaves sialic acid residues from sialic acid α(2,6) β-N-acetylgalactosamine residues, the binding of PSA to TJA-II or WFA is increased and it is possible to efficiently distinguish between PSA from prostate cancer patient serum and PSA from prostatic hypertrophy patient serum. More particularly, the present inventors have found that serum PSA from most prostate cancer patients has sialic acid α(2,6) β-N-acetylgalactosamine residues (Siaα2→6GalNAcβ1→R), and the β-N-acetylgalactosamine residues (GalNAcβ1→R) were exposed by removing sialic acid residues using a sialidase, and thereby the PSA can be effectively bound to TJA-II or WFA.

The present invention is based on the above findings.

Solution to Problem

A method for analyzing PSA characterized in that a lectin having an affinity for β-N-acetylgalactosamine residues is brought into contact with a sample possibly containing PSA, to determine an amount of PSA having an affinity for the lectin is disclosed in the present specification.

The method for analyzing PSA according to a preferable embodiment of the present invention comprises the steps of (a) bringing the lectin having an affinity for a β-N-acetylgalactosamine residue into contact with the sample, to separate PSA having an affinity for the lectin from PSA lacking an affinity for the lectin; (b) determining the amount of PSA having an affinity for the lectin.

The present invention relates to a method for analyzing PSA characterized in that a lectin having an affinity for β-N-acetylgalactosamine residues is brought into contact with a sialidase-treated sample obtained by adding a sialidase to the sample possibly containing PSA, to determine an amount of PSA having an affinity for the lectin.

The method for analyzing PSA according to a preferable embodiment of the present invention comprises the steps of (s) adding sialidase to the sample possibly containing PSA, to obtain the sialidase-treated sample; (a) bringing the lectin having an affinity for β-N-acetylgalactosamine residues into contact with the sialidase-treated sample, to separate a PSA having an affinity for the lectin from a PSA lacking an affinity for the lectin; (b) determining the amount of PSA having an affinity for the lectin.

According to a preferable embodiment of the method for analyzing PSA of the present invention, the amount of PSA having an affinity for the lectin is determined (1) by measuring an amount of separated PSA having an affinity for the lectin, (2) by measuring an amount of PSA in a sample before the separation and an amount of the separated PSA having an affinity for the lectin, or (3) by measuring an amount of PSA in a sample before the separation and an amount of the separated PSA lacking an affinity for the lectin.

According to a preferable embodiment of the method for analyzing PSA of the present invention, the amount of PSA is determined by measuring total PSA or free PSA.

According to a preferable embodiment of the method for analyzing PSA of the present invention, the lectin is *Trichosanthes japonica* agglutinin-II or *Wisteria floribunda* agglutinin.

According to another preferable embodiment of the method for analyzing PSA of the present invention, the lectin further has an affinity for fucose $\alpha(1,2)$ galactose residues.

According to a preferable embodiment of the method for analyzing PSA of the present invention, the sample is obtained from a patient suspected of having prostate cancer.

A method for analyzing PSA according to a preferable embodiment of the present invention is for diagnosis of prostate cancer.

Further, the present invention relates to a method for analyzing PSA characterized in that a lectin having an affinity for $\beta$-N-acetylgalactosamine residues and a lectin having an affinity for fucose $\alpha(1,2)$ galactose residues are brought into contact with a sialidase-treated sample obtained by adding sialidase to a sample possibly containing PSA, to determine an amount of PSA having an affinity for the lectin.

A method for analyzing PSA according to a preferable embodiment of the present invention comprises the steps of (s) adding sialidase to the sample possibly containing PSA, to obtain the sialidase-treated sample; (a) bringing the lectin having an affinity for $\beta$-N-acetylgalactosamine residues and the lectin having an affinity for fucose $\alpha(1,2)$ galactose residues into contact with the sialidase-treated sample, to separate PSA having an affinity for the lectin from PSA lacking an affinity for the lectin; (b) determining the amount of PSA having an affinity for the lectin.

The present invention relates to a method for distinguishing prostate cancer from prostatic hypertrophy, characterized in that the amount of PSA having an affinity for a lectin in a sample is analyzed by the method for analyzing PSA.

The present invention relates to an analysis kit of PSA comprising a lectin having an affinity for $\beta$-N-acetylgalactosamine residues.

An analysis kit of PSA according to a preferable embodiment of the present invention further comprises sialidase.

An analysis kit of PSA according to a preferable embodiment of the present invention further comprises an anti-PSA antibody.

According to a preferable embodiment of the analysis kit of PSA of the present invention, the lectin is *Trichosanthes japonica* agglutinin-II or *Wisteria floribunda* agglutinin.

Further, according to a preferable embodiment of the analysis kit of PSA of the present invention, the lectin further has an affinity for fucose $\alpha(1,2)$ galactose residues.

An analysis kit of PSA according to a preferable embodiment of the present invention comprises a lectin having an affinity for $\beta$-N-acetylgalactosamine residues and a lectin having an affinity for fucose $\alpha(1,2)$ galactose residues.

An analysis kit of PSA according to a preferable embodiment of the present invention further comprises a sialidase.

The present invention relates to a method for detecting the prostate cancer characterized in that an expression level of fucosyltransferase 1 or $\beta$-N-acetylgalactosaminyltransferase 4 in a sample derived from a living body is analyzed.

According to a preferable embodiment of the method for detecting the prostate cancer of the present invention, an expression level of mRNA of fucosyltransferase 1 or $\beta$-N-acetylgalactosaminyltransferase 4 is analyzed.

According to a preferable embodiment of the present invention, an antibody specifically binding to fucosyltransferase 1 or $\beta$-N-acetylgalactosaminyltransferase 4 is used.

The present invention relates to a kit for detecting a prostate cancer characterized by comprising primer sets and/or a probe which are specific for mRNA of fucosyltransferase 1 or $\beta$-N-acetylgalactosaminyltransferase 4.

Further, a kit for detecting a prostate cancer characterized by comprising an antibody specifically binding to fucosyltransferase 1 or $\beta$-N-acetylgalactosaminyltransferase 4, or a fragment thereof.

Advantageous Effects of Invention

According to the method for analyzing PSA, the method for distinguishing prostate cancer from prostatic hypertrophy and the analysis kit of PSA, prostate cancer can be clearly distinguished from prostatic hypertrophy. Further, TJA-II, WFA, and UEA-I can be used in the present invention, and the PSA bound to the lectins can be recovered at a recovery rate of about 100%. Therefore, a quantity of PSA from prostate cancer patient serum having $\beta$-N-acetylgalactosamine residues can be measured precisely. Furthermore, TJA-II, WFA and UEA-I columns are reproducible, and reusable.

DESCRIPTION OF EMBODIMENTS

[1] A Method for Analyzing PSA

Figure 1:
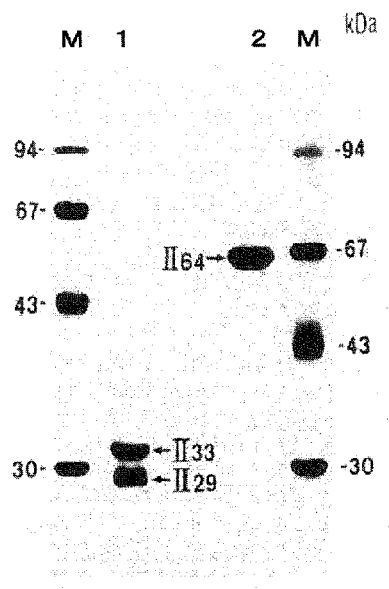
FIG. 1 is a photograph showing the results obtained by electrophoresing a purified TJA-II. M shows a molecular weight marker. Lane 1 shows reduced TJA-II. Lane 2 shows nonreduced TJA-II.

A method for analyzing PSA of the present invention is characterized in that a lectin having an affinity for β-N-acetylgalactosamine residues is brought into contact with a sample possibly containing PSA, to determine the amount of PSA having an affinity for the lectin. More particularly, according to a preferable embodiment of the present invention, the method for analyzing PSA is characterized in that the lectin having an affinity for β-N-acetylgalactosamine residues is brought into contact with a sialidase-treated sample obtained by adding a sialidase to the sample possibly containing PSA, to determine the amount of PSA having an affinity for the lectin. Alternatively, according to another embodiment of the present invention, a method for analyzing PSA is characterized in that a lectin having an affinity for fucose α(1,2) galactose residues is brought into contact with a sample possibly containing PSA, to determine the amount of PSA having an affinity for the lectin.

An example of a lectin which may be used in the present invention is a lectin having an affinity for β-N-acetylgalactosamine residues (GalNAcβ1→R) linked to a nonreducing terminal. In this case, β-N-acetylgalactosamine of a nonreducing terminal must not be substituted by sialic acid and sulfuric acid. The lectin having an affinity for the β-N-acetylgalactosamine residues includes, but is not limited to, TJA-II or WFA.

A further example of a lectin which may be used in the present invention is a lectin having an affinity for fucose α(1,2) galactose residues (Fucα1→2Galβ1→R). The fucose α(1,2) galactose residue is a terminal carbohydrate chain having a structure wherein α-fucose is bound to galactose at the C-2 position. The lectin having an affinity for the β-N-acetylgalactosamine residues includes, but is not limited to, UEA-I or TJA-II.

A further example of a lectin which may be used in the present invention is a lectin having an affinity for β-N-acetylgalactosamine residues (GalNAcβ1→R) and fucose α(1,2) galactose residues bound to a nonreducing terminal. Among the PSA of a prostate cancer patients, there may exist PSA expressing β-N-acetylgalactosamine residues only or PSA expressing fucose α(1,2) galactose residues only. Furthermore, there is a high possibility that PSA in a prostate cancer patient expresses dominantly either β-N-acetylgalactosamine residues or fucose α(1,2) galactose residues. Therefore, in the method for analyzing PSA according to the present invention, the lectin having an affinity for β-N-acetylgalactosamine residues (GalNAcβ1→R) bound to a nonreducing terminal and fucose α(1,2) galactose residues bound to a nonreducing terminal is preferably used. The lectin having an affinity for β-N-acetylgalactosamine residues (GalNAcβ1→R) and fucose α(1,2) galactose residues bound to the nonreducing terminal includes, but is not limited to, TJA-II.

TJA-II is extracted from a tuberous root of *Trichosanthes japonica* and purified. The molecular weight determined by electrophoresis in the non-reduced condition is 64 kDa. The molecular weight by electrophoresis in the reduced condition is 32 kDa and 29 kDa because TJA-II is dimer having disulfide bond. TJA-II exhibits a strong affinity for β-N-acetylgalactosamine residues (GalNAcβ1→R) and fucose α(1,2) galactose residues (Fucα1→2Galβ1→R).

WFA is extracted from seeds of *Wisteria floribunda* and purified. WFA exhibits a strong affinity for β-N-acetylgalactosamine residues (GalNAcβ1→R) to itself. Further, WFA also exhibits a strong affinity for a GalNAcβ1→4Gal residue and a GalNAcβ1→4GlcNAc residue.

UEA-I (Ulex europaeus agglutinin-1) is a lectin prepared from Ulex europaeus, and the molecular weight is approximately 26,700 Da. UEA-I has a carbohydrate binding specificity against α-L-Fuc and exhibits a strong affinity for a fucose α(1,2) galactose residues (Fucα1→2Galβ1→4GlcNAc→R).

In the method for analyzing PSA according to the present invention, the lectin having an affinity for 3-N-acetylgalactosamine residues, the lectin having an affinity for fucose α(1,2) galactose residues, and the lectin having an affinity for both β-N-acetylgalactosamine residues and fucose α(1,2) galactose residues may be used alone or in combinations of two or more.

As the lectin used in the present invention, a commercially available lectin can be used, and further a lectin purified in accordance with conventional methods can also be used. A plant body, such as leaf, stem, flower, root, seed, or the like is scrapped, crushed, and dissolved in a buffer solution. A supernatant is collected by centrifugal separation, and then a lectin can be purified from the supernatant using ammonium sulfate precipitation, ion-exchange column chromatography, hydrophobic column chromatography, gel filtration column chromatography, affinity column chromatography, dialysis, lyophilization, or the like. Particularly, TJA-II can be purified in accordance with the report of Yamashita et al. (Yamashita et al., J. Biol. Chem., 267, 25441-25422, 1992). Further, WFA can be purified in accordance with the report of Toyoshima et al. (Toyoshima et al., Biochemistry, 10, 4457-4463, 1971). Furthermore, UEA-I can be purified in accordance with the report of Hindsgaul et al. (Hindsgaul et al., Carbohydr. Res., 109, 109-142, 1982).

The sialidase which can be used in the present invention is not particularly limited, so long as α(2→6) binding of a sialic acid can be cleaved. In PSA of a prostate cancer patient, sialic acid residues are bound to β-N-acetylgalactosamine residues by α(2→6) linkage. Therefore, β-N-acetylgalactosamine residues are exposed by cleaving α(2→6) binding of sialic acid residues, and then the PSA can be bound to the lectin having an affinity for β-N-acetylgalactosamine residues (GalNAcβ1→R).

The linkages of sialic acid residues include α(2→3) binding, α(2→6) binding and α(2→8) binding. As the sialidase which can be used in the present invention, a sialidase which may cleave α(2→6) binding only or a sialidase which may cleave any bindings including α(2→6) binding can be used. For example, since a sialidase derived from *Arthrobacter ureafaciens* can cleave α(2→3) binding, α(2→6) binding and α(2→8) binding, the sialidase can be used in the method for analyzing PSA in the present invention.

The sialidase is called a neuraminidase, and mammals also have sialidases. The study of sialidases derived from bacteria, a virus and a protozoan has been advanced. A sialidase derived from *Arthrobacter ureafaciens, Clostridium perfringens, Salmonella typhimurium*, influenza virus, Newcastle disease virus, or the like is known as a sialidase. Of these, examples of the sialidase which can cleaved α(2→6) binding of sialic acid residues are sialidases derived from *Arthrobacter ureafaciens* and *Clostridium perfringens*.

The method for analyzing PSA described herein is not particularly limited, so long as the lectin is brought into contact with a sample possibly containing PSA, to determine the amount of PSA having an affinity for the lectin. Examples of the method for analyzing PSA include (A) a method for separating PSA having an affinity for the lectin from PSA lacking an affinity for the lectin to determine the amount of PSA having an affinity for the lectin (hereinafter sometimes referred to as an analytical method (A)) and (B) a method for determining the amount of PSA having an affinity for the lectin on the condition that the lectin is bound to PSA having an affinity for the lectin (hereinafter sometimes referred to as an analytical method (B)). Examples of a method for analyzing PSA according to the present invention include (sA) a method using a sialidase-treated sample, obtained by adding sialidase to a sample possibly containing PSA, as a sample in the analytical method (A) (hereinafter sometimes referred to as an analytical method (sA)) and (sB) a method using a sialidase-treated sample, obtained by adding sialidase to a sample possibly containing PSA, as a sample in the analytical method (B) (hereinafter sometimes referred to as an analytical method (sB)). Analytical method (A) includes the analytical method (sA) and the analytical method (B) includes the analytical method (sB), respectively.

Analytical Method (A)

The analytical method (A) comprises
(a) a step of bringing a lectin having an affinity for β-N-acetylgalactosamine residues (as a lectin used in the present invention) into contact with a sample possibly containing PSA, to separate PSA having an affinity for the lectin from PSA lacking an affinity for the lectin (hereinafter sometimes referred to as the separation step (a)), and
(b) a step of determining the amount of PSA having an affinity for the lectin in the sample (hereinafter sometimes referred to as the determination step (b)).

Analytical Method (sA)

An analytical method (sA) according to the present invention is included in the analytical method (A), and comprises (s) a step of obtaining a sialidase-treated sample by adding a sialidase to a sample possibly containing PSA before a separation step (a) in the analytical method (A) (hereinafter sometimes referred to as sialidase treatment step (s)).

More particularly, an analytical method (sA) comprises the steps of
(s) adding a sialidase to a sample possibly containing PSA, to obtain a sialidase-treated sample;
(a) bringing the lectin having an affinity for β-N-acetylgalactosamine residues into contact with the sialidase-treated sample, to separate PSA having an affinity for the lectin from PSA lacking an affinity for the lectin;
(b) determining the amount of PSA having an affinity for the lectin.

In the sialidase treatment step (s), a sample possibly containing PSA may or may not be diluted in a suitable buffer solution, and then a sialidase capable of cleaving the α(2→6) binding of sialic acid residues is added to the sample. Thereby, sialic acid is removed from PSA and, as a result, β-N-acetylgalactosamine residues of the PSA can be exposed.

The buffer for diluting the sample is not limited, so long as it can maintain an activity of the sialidase. For example a phosphate buffer containing 0.1% bovine serum albumin (BSA), a Tris-HCl buffer containing 0.1% bovine serum albumin (BSA) or the like, which are used for equilibrating of the above lectin column, can be used.

The amount of the sialidase used is not limited, and may be decided in accordance with the type of sialidase. For example, when the sialidase derived from *Arthrobacter ureafaciens* is used, α(2→6) binding of sialic acid of PSA can be cleaved by the use of 2 to 1000 mU, preferably 10 to 500 mU, more preferably 20 to 100 mU of the sialidase.

The incubation time (reaction time) of the sialidase is not limited, and may be decided in accordance with the type of sialidase. The treating time is 10 minites to 24 hours, preferably 15 minites to 2 hours, more preferably 30 minites to 1 hour. In addition, the reaction temperature of the sialidase is not limited, and may be decided in accordance with the type of sialidase. The reaction temperature is preferably 25° C. to 40° C.

The sialidase-treated sample obtained in the sialidase treatment step (s) may be used as it is or as further diluted in the separation step (a), and subsequently the determination step (b) may be performed.

The method of separating PSA having an affinity for the lectin from PSA lacking an affinity for the lectin in separation step (a) is not particularly limited as long as it is a method utilizing an affinity of PSA for the lectin. For example, the method may be performed by binding a lectin to a carrier (hereinafter, sometimes referred to as a "lectin affinity column"), bringing the carrier into contact with a sample possibly containing PSA, and separating PSA bound to the lectin from PSA not bound to the lectin.

The carrier is not limited as long as it can be bound to a lectin. Examples of the carrier include sepharose, cellulose, agarose, dextran, polyacrylate, polystyrene, polyacrylamide, polymethacrylamide, copolymer of styrene and divinylbenzene, polyamide, polyester, polycarbonate, polyethyleneoxide, hydroxypropyl methylcellulose, polyvinyl chloride, polymethylacrylate, copolymer of polystyrene and polystyrene, polyvinyl alcohol, polyacrylic acid, collagen, calcium alginate, latex, polysulfone, silica, zirconia, alumina, titania and ceramics. The form of the carrier is not also particularly limited, but includes particulate bead, microtiter plate, gel and the like. For example, if a lectin affinity column is used in separation of PSA having an affinity for a lectin from PSA lacking an affinity for a lectin, the carrier preferably has the gel form.

The lectin affinity column may be prepared according to standard procedures. For example, the lectin column may be prepared by performing coupling using CNBr-activated Sepharose 4B according to the protocol recommended by the manufacturer. The binding amount of the lectin to the sepharose gel is preferably from 2 mg/mL to 10 mg/mL.

The method of separating PSA having an affinity for the lectin from PSA lacking an affinity for the lectin using the lectin affinity column may be performed according to a conventional method of separating glycoprotein using lectin affinity columns.

The lectin affinity column is equilibrated with a buffer before application of a sample possibly containing PSA. Examples of the equilibration buffer include a phosphate buffer containing 0.1% bovine serum albumin (BSA), and a Tris-HCl buffer containing 0.1% bovine serum albumin (BSA).

After equilibration of the column, a sample possibly containing PSA is added thereto, and allowed to stand for a predetermined time, to bring the lectin and PSA into contact. The contact time is not particularly limited, and may be properly decided according to the kinds of lectin and their PSA affinity. However, considering the binding rate and the efficiency, the contact is usually performed for 15 minutes to 30 minutes.

The temperature where lectin and PSA are brought into contact is not also particularly limited, but may be properly decided according to the kinds of lectin and their affinity with PSA. However, the contact may be performed at 0° C. to 40° C., preferably at 0° C. to 30° C. If the temperature is lower than 0° C., the column may freeze, and if the temperature is higher than 40° C., non-specific binding of a protein lacking an affinity for the lectin may occur. For example, the temperature where TJA-II and PSA are brought into contact is not particularly limited. However, they are brought into contact at preferably from 4° C. to 10° C. In addition, the temperature where WFA and PSA are brought into contact is also not particularly limited. However, they are brought into contact at preferably from 4° C. to 10° C.

Next, the bound molecules having an affinity for the lectin (hereinafter, sometimes referred to as a "the bound molecules") are separated from the non-bound molecules lacking an affinity for the lectin (hereinafter, sometimes referred to as a "the non-bound molecules").

The non-bound molecules can be obtained by adding a washing buffer to a column, and recovered in the passed-through fractions. The washing buffer is not limited as long as it is a buffer that runs off the non-bound molecules without dissociating the binding of the lectin and PSA. For example, the buffer used in the equilibration may be used as the washing buffer. The volume of the washing buffer may be properly decided depending on the kinds of lectin and affinity with PSA. However, the volume is preferably about 3 to 7 times, more preferably about 5 times the volume of the column.

The bound molecules can be obtained by adding an elution buffer to a column, and recovered in the eluted fractions. The elution buffer contains a haptenic sugar, with which PSA bound to a lectin can be eluted from the lectin. The haptenic sugar may be selected properly in accordance with carbohydrate binding specificity of the lectin. If the lectin is TJA-II, lactose and the like may be used as the haptenic sugar. For example, the bound molecules can be recovered using a phosphate buffer containing 10 mM lactose and 0.1% bovine serum albumin (BSA). In addition, if the lectin is WFA, N-acetylgalactosamine (GalNAc) and the like may be used as the haptenic sugar. For example, the bound molecules can be recovered using a phosphate buffer containing 10 mM GalNAc and 0.1% bovine serum albumin (BSA). The volume of the elution buffer may be selected properly, but is preferably about 3 to 7 times, more preferably about 5 times the volume of the column. The temperature of the elution is not also particularly limited. However, the elution may be performed at 0° C. to 40° C., preferably 2 to 25° C., and more preferably 4 to 20° C. If the temperature is lower than 0° C., the column may freeze, and if the temperature is higher than 40° C., non-specific binding of a protein lacking an affinity for a lectin may occur. For example, the temperature which PSA is eluted from TJA-II is not particularly limited. However, the elution is preferably performed at room temperature. In addition, the temperature which PSA is eluted from WFA is not also particularly limited. However, the elution is preferably performed at room temperature.

In the determination step (b), determination of the amount of PSA having an affinity for the lectin includes (1) Determination by measuring the amount of separated PSA having an affinity for the lectin, (2) Determination by measuring the amount of PSA in the sample before the separation, and by measuring the amount of the separated PSA having an affinity for the lectin, or (3) Determination by measuring the amount of PSA in the sample before the separation, and by measuring the amount of the separated PSA lacking an affinity for the lectin.

The determination (1) by measuring the amount of separated PSA having an affinity for the lectin may be performed by measuring the PSA amount in the binding fractions quantitatively or semi-quantitatively. In other words, the determination is performed by measuring the absolute amount of PSA having an affinity for the lectin contained in the blood of a patient.

The determination (2) by measuring the amount of PSA in the sample before the separation, and measuring the amount of the separated PSA having an affinity for the lectin, may be performed by comparing the PSA amount in the sample before the separation (or the total amounts of PSA in the binding fractions and the non-binding fractions) with the amount of PSA in the binding fractions to the lectin. Specifically, the amount of PSA having an affinity for the lectin can be determined by calculating the ratio of the amount of PSA in the binding fractions, to the amount of PSA in the sample before separation (or the total of the amount of PSA in the binding fractions and the non-binding fractions), and for example, can be calculated by either of the equations below.

Binding rate of PSA=(amount of PSA in the binding fraction/total amount of PSA in the binding fraction and the non-binding fraction)×100%

Binding rate of PSA=(amount of PSA in the binding fraction/PSA amount in the sample before a separation)×100%

In addition, the determination (3) by measuring the amount of PSA in the sample before a separation, and measuring the amount of separated PSA lacking an affinity for a lectin, may be performed by comparing the amount of PSA in the sample before a separation (or the total of the amount of PSA in the binding fractions and the non-binding fractions) with the amount of PSA in the non-binding fractions. Specifically, the amount of PSA having an affinity for the lectin can be determined by subtracting the amount of PSA in the non-binding fractions from the amount of PSA in the sample before separation (or the total of the amount of PSA in the binding fractions and the non-binding fractions). For example, the amount of PSA having an affinity for the lectin can be calculated by any of the equations below.

Amount of PSA having an affinity for a lectin=amount of PSA in the sample before a separation−amount of PSA in the non-binding fraction Amount of PSA having an affinity for a lectin=Total amount of PSA in the binding fraction and the non-binding fraction−amount of PSA in the non-binding fraction In the determinations (1) and (2), the amount of PSA bound to a lectin is measured after separating bound PSA from the lectin. However, in the determination (3), which is the determination from the amount of PSA in the sample before a separation and the amount of PSA in the non-binding fractions, the amount of PSA bound to a lectin is not measured, and thus the amount of PSA bound to a lectin may be determined without separating PSA bound to a lectin.

In addition, regarding obtaining the amount of PSA in the binding fractions and non-binding fractions separately, the measurement of the amount of PSA is preferably performed for all of the fractions. However, the fractions containing PSA are preliminarily analyzed and the amount of PSA can be determined by measuring the fractions of interest.

In the determination step (b), the method of measuring PSA in order to determine the amount of PSA having an affinity for a lectin, is not particularly limited as long as it is a method that allows quantitative or semi-quantitative determination of PSA. Examples of the method of measuring PSA include a method of measuring total PSA and a method of measuring free PSA. The method of measuring total PSA or the method of measuring free PSA may be performed by immunological techniques using antibody or a fragment thereof (for example, enzyme immunoassay, latex agglutination immunoassay, chemiluminescent immunoassay, fluorescent antibody method, radioimmunoassay, immunoprecipitation method, immunohistological staining method, or the western blot) according to standard procedures. Commercially available PSA measurement kits may also be used.

In the case where the immunological assay is used as the method of measuring total PSA, a monoclonal antibody or a polyclonal antibody is used that can bind to both PSA-ACT and free PSA. On the other hand, in the case where the immunological assay is used as the method of measuring free PSA, a monoclonal antibody or a polyclonal antibody is used that can bind only to free PSA. The monoclonal antibody or the polyclonal antibody can be prepared by a known method except that PSA-ACT or free PSA is used as an immunizing antigen. For example, the monoclonal antibody can be prepared according to Koehler and Milstein's method (Nature 256: 495-497, 1975). In addition, the polyclonal antibody can be prepared by conventional immunization with an antigen that is PSA-ACT or free PSA as alone or as bound to BSA, KLH and the like, which is mixed with an adjuvant such as simple adjuvant or Freund's complete adjuvant, for example, in the skin of a rabbit. The blood is collected at the time when the antibody titer increases, which may be utilized as it is as an antiserum, or the antibody may be used as purified by a known method.

By the analysis of Examples described below, it was found that the lectin affinity column using TJA-II or WFA, which may be used in the method for analyzing PSA of the present invention, can recover about 100% (at least 97% or more) of PSA in the sample. In comparison to this, with MAA described in Patent Reference 1, the recovery rate was 30 to 70% when using a phosphate buffer containing 0.4M lactose as an eluting solution, and the recovery rate did not improve even if the eluting solution was changed to 0.1 M acetic acid solution.

Analysis Method (B)

The analysis method (B) is a method wherein PSA having an affinity for a lectin is directly detected by the lectin. Specifically, analysis method (B) includes the lectin blot analysis by electrophoresis, or the lectin blot analysis by dot blotting. Any one of the lectin blot analyses may be performed according to standard procedures. With the lectin blot analysis by electrophoresis, a sample possibly containing PSA is subjected to electrophoresis, and PSA is transferred to a nitrocellulose membrane or a PVDF membrane, which is used as a sample membrane. With the lectin blot analysis by dot blotting, a sample possibly containing PSA is adsorbed onto a nitrocellulose membrane or a PVDF membrane by a dot blotting apparatus, and the membrane is used as a sample membrane. Blocking is performed with a blocking buffer for the sample membrane, and the sample membrane is brought into contact with a solution containing a biotin-labeled lectin, for example biotin-labeled WFA or biotin-labeled TJA-II. Then, the sample membrane is brought into contact with avidin labeled with an enzyme such as HRP or ALP, and then brought into contact with solution containing a chromogenic or a luminescent enzyme substrate, and the obtained signal is detected.

Furthermore, method (B) of directly detecting PSA having an affinity for a lectin by the lectin may be performed by the immunoblot analysis and the enzyme immunoassay with partial modification. Specifically, the monoclonal antibody or polyclonal antibody for PSA is immobilized on a nitrocellulose membrane or an ELISA plate, and blocking is performed with a blocking buffer. The sample possibly containing PSA is brought into contact with the nitrocellulose membrane or the ELISA plate, and then, brought into contact with a biotin-labeled lectin, for example biotin-labeled WFA or biotin-labeled TJA-II. Then, the sample is bound to avidin labeled with an enzyme such as HRP or ALP, and then the signal can be detected following incubation with a solution containing a chromogenic or a luminescent enzyme substrate.

Analysis Method (sB)

The analysis method (sB) of the present invention, which is included in analysis method (B), includes step (s) in which sialidase is added to a sample possibly containing PSA, to obtain a sialidase-treated sample (i.e., the sialidase treatment step (s)) before the lectin blotting following electrophoresis, or dot blotting. The sialidase treatment step (s) may be performed in the same manner as the step described in the analysis method (sA), and the obtained sialidase-treated sample may be used in the lectin blot analysis as it is, or after further dilution.

Examples of the sample used in the method for analyzing PSA of the present invention include PSA-containing biological samples, or samples derived from human body, and biological samples isolated or derived from the human body possibly containing PSA. Examples of the sample to be tested include urine, blood, serum, plasma, spinal fluid, saliva, cell, tissue or organ, and preparations thereof (for example, a biopsy sample, particularly a prostatic biopsy sample). The sample to be tested is preferably blood, serum, plasma, or a prostatic biopsy sample, particularly preferably blood, serum, or plasma. Blood, serum, or plasma is appropriate as a sample to be tested for detecting the prostate cancer, because PSA having β-N-acetylgalactosamine residues and/or fucose α(1,2) galactose residues is released into the blood in the initial stage of disease in prostate cancer patients, whereas little PSA having β-N-acetylgalactosamine residues and/or fucose α(1,2) galactose residues exists in the blood, serum, or plasma of normal healthy subjects and prostatic hypertrophy patients.

A liquid sample such as urine, blood, serum, plasma, spinal fluid and saliva may be used as diluted in the analysis method (A) or the analysis method (B) with an appropriate buffer depending on each of the analysis methods. In addition, a solid sample such as cell, tissue or organ is homogenized with an appropriate buffer in an amount about 2 to 10 times the volume of the solid sample, and a suspension or a supernatant thereof may be used in the analysis method (A) or the analysis method (B) as it is, or after further dilution.

For example, if the lectin affinity column is used in analysis method (A), the liquid sample, or a suspension of the solid sample or a supernatant thereof may be used as diluted with an appropriate buffer. The dilution rate is not particularly limited as long as it does not inhibit the binding of PSA to the lectin. However, the dilution rate is preferably 2 to 400 times, more preferably 2 to 300 times, and most preferably 4 to 200 times. In addition, the volume of the sample applied to the lectin affinity column is preferably equal to or less than 40%, more preferably equal to or less than 30%, and most preferably equal to or less than 20% of the bed volume of the column. For example, if 1 mL bed volume of the lectin affinity column is used, the volume of the sample applied to the lectin affinity column is preferably equal to or less than 400 μL, more preferably equal to or less than 300 μL, and most preferably equal to or less than 200 μL.

[2] Method for Distinguishing Prostate Cancer from Prostatic Hypertrophy

It is possible to distinguish between prostate cancer and prostatic hypertrophy by analyzing the amount of PSA having an affinity for a lectin in a sample by the method for analyzing PSA.

It is possible to determine whether the patient has the prostate cancer or not by measuring the amount of PSA having an affinity for the lectin by the method for analyzing PSA, and comparing that with the amount of PSA having an affinity for the lectin in the blood or the like collected from prostatic hypertrophy patients or normal healthy subjects. More specifically, it is possible to determine that the patient has the prostate cancer if there is significantly more PSA having an affinity for a lectin existing in the sample of the patient than there is in the samples of prostatic hypertrophy patients or normal healthy subjects.

In the analysis method (A) (including the analysis method (sA)), the binding rate to TJA-II, which recognizes β-N-acetylgalactosamine residues and fucose α(1,2) galactose residues, is different from the binding rate to WFA, which recognizes only β-N-acetylgalactosamine residues. Accordingly, it is preferable to decide the cutoff values that allow distinction between prostate cancer and prostatic hypertrophy by the measurement value of the used lectin. The cutoff value is most preferably a value that allows determination of prostate cancer patients as positive by 100%, and determination of prostatic hypertrophy patients as negative by 100%. If the measurement values are overlapped between the prostate cancer patients and the prostatic hypertrophy patients in accordance with increases of the analyzed population of prostate cancer and prostatic hypertrophy, it is preferable to select a value that allows 100% judgment of the prostate cancer patients as positive as the cutoff value. However, it is also possible to select any value in the overlapped range as the cutoff value. Specifically, if the amount of PSA in the TJA-II binding fraction is measured as described below in examples, the cutoff value for detecting prostate cancer patients is not limited as long as it is a value that allows detection of PSA of the prostate cancer patients, but can be set as, for example, some value between 200 pg/mL and 240 pg/mL, preferably 220 pg/mL.

In addition, the binding rate of PSA to a lectin in Examples described below may be decided from the percentage that can be obtained in the following equation.

Binding rate of PSA=(amount of PSA in the binding fraction/amount of PSA amount in the sample before a separation)×100%

The cutoff value of the binding rate of PSA is also most preferably a value that allows determination of prostate cancer patients as positive by 100%, and determination of prostatic hypertrophy patients as negative by 100%. If the binding rates of PSA to the lectin are overlapped between the prostate cancer patients and the prostatic hypertrophy patients in accordance with increases of the analyzed population of prostate cancer and prostatic hypertrophy, it is preferable to select a value that allows 100% judgment of the prostate cancer patients as positive as the cutoff value. However, it is also possible to select any value in the overlapped range as the cutoff value. Specifically, the cutoff value of the TJA-II binding rate of PSA in Examples described below is not limited as long as it is a value that allows detection of the prostate cancer, but can be set up as, for example, a value between 1.8% and 3%, preferably 2.4%.

[3] Diagnosis Kit for Prostate Cancer

The diagnosis kit of the present invention contains a lectin having an affinity for β-N-acetylgalactosamine residues. In addition, the diagnosis kit of the present invention may also contain a lectin having an affinity for fucose α(1,2) galactose residues. The diagnosis kit of the present invention may contain a lectin having an affinity for β-N-acetylgalactosamine residues (GalNAcβ1→R) and fucose α(1,2) galactose residues. The lectin contained in the diagnosis kit of the present invention also includes those bound to the above-mentioned carriers.

The diagnosis kit of the present invention may contain a lectin having an affinity for β-N-acetylgalactosamine residues, a lectin having an affinity for fucose α(1,2) galactose residues, or a lectin having an affinity for β-N-acetylgalactosamine residues and fucose α(1,2) galactose residues, alone or in a combination of two or more.

The lectin having an affinity for β-N-acetylgalactosamine residues is not particularly limited, but includes TJA-II or WFA. In addition, the lectin having an affinity for fucose α(1,2) galactose residues is not particularly limited, but includes UEA-1 or TJA-II. Furthermore, the lectin having an affinity for β-N-acetylgalactosamine residues (GalNAcβ1→R) and fucose α(1,2) galactose residues includes TJA-II.

The diagnosis kit of the present invention may also contain a sialidase. The sialidase is not particularly limited as long as it is sialidase that can cleave the Siaα(2→6)Gal residues. The sialidase includes sialidases derived from *Arthrobacter ureafaciens* and *Clostridium perfringens*.

The diagnosis kit of the present invention may further contain an anti-PSA antibody (for example, antibody specifically binding to PSA-ACT or free PSA) or a fragment thereof. As the antibody, any of monoclonal antibody or polyclonal antibody may be used. The antibody fragment is not particularly limited as long as it has specific binding ability to PSA-ACT or free PSA, and appropriate fragments include, for example, Fab, Fab', F(ab')$_2$, or Fv.

The diagnosis kit of the present invention containing the lectin and the anti-PSA antibody, may contain the anti-PSA antibody or a fragment thereof in a desired form depending on the immunological technique used.

For example, in a case where an immunological technique using a labeled antibody is used such as enzyme immunoassay detected by fluorescence, chemiluminescence, or radioactivity, the diagnosis kit may contain the anti-PSA antibody or a fragment thereof in a form of a labeled antibody or a labeled antibody fragment conjugated with a labeling substance. Specific examples of the labeling substance include enzymes such as peroxidase (HRP), alkaline phosphatase (ALP), β-D-galactosidase or glucose oxidase, fluorescent substances such as fluorescein isothiocyanate or rare-earth metal chelate, radioactive isotopes such as $^3$H, $^{14}$C or $^{125}$I, and miscellaneously, biotin, avidin, and chemiluminescent substances. In the case where the antibodies labeled with enzymes such as HRP, ALP or the like is used, they preferably contain an appropriately selected substrate and the like since they cannot generate measurable signal by themselves.

Function

For patients exhibiting a gray PSA value (the total PSA value is 4 to 10 ng/mL), measurement of the free PSA/total PSA ratio (F/T value) of the serum sample is performed as described above. As shown in Table 1, the F/T value is equal to or less than 25% in 7 out of 9 of the prostatic hypertrophy patients. The seven patients are subjects of biopsy for confirmed diagnosis, but in fact, they have prostatic hypertrophy, and thus such biopsy for confirmed diagnosis is excessive burden to the patients.

Figure 6:
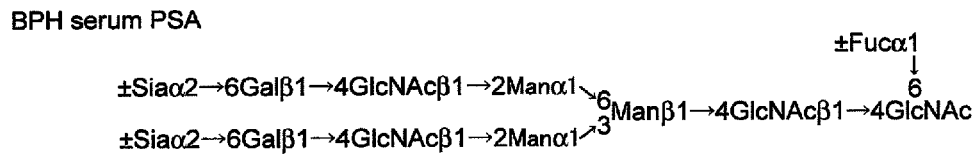
FIG. 6 is a view showing the carbohydrate structures of PSA in the serum sample of a prostate cancer patient (PC serum PSA) and PSA in the serum sample of a prostatic hypertrophy patient (BPH serum PSA).
Figure 6:
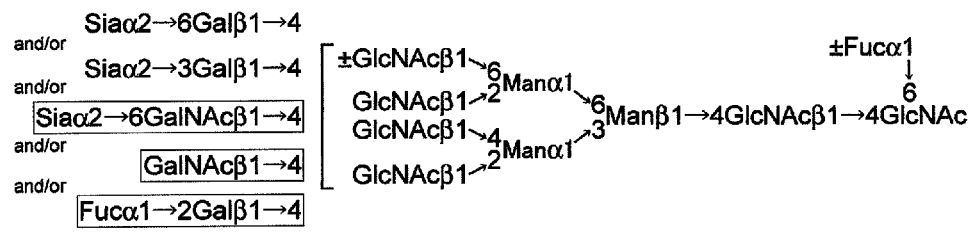

TJA-II, which may be used in the present invention is a lectin that recognizes fucose α(1,2) galactose residues and β-N-acetylgalactosamine residues existing at the non-reducing terminal of the sugar chain. WFA is a lectin that recognizes β-N-acetylgalactosamine residues existing at the non-reducing terminal of the sugar chain. UEA-I is a lectin that recognizes fucose α(1,2) galactose residues existing at the non-reducing terminal of the sugar chain. It is shown for the first time by the present specification that PSA which can bind to TJA-II, WFA or UEA-I exists in the body of the prostate cancer patient, i.e., these sugar chain structures appear in PSA with canceration as shown in FIG. 6.

Furthermore, it was found as shown in Example 3 described below that the amount of PSA that can bind to TJA-II increases by treating the serum PSA of the prostate cancer patient with sialidase that can cleave an α(2,6) binding of sialic acid. This indicated that a β-N-acetylgalactosamine residue to which the sialic acid bound is exposed by the sialidase treatment. In other words, it was found for the first time that PSA contained in the serum of a prostate cancer patient has a sialic acid α(2,6) β-N-acetylgalactosamine residue (Siaα2→6GalNAcβ1→R) as shown in FIG. 6.

As described above, it has been reported that PSA of LNCaP cells has a HexNAcβ1-HexNAc residue on the side of the non-reducing terminal (Non-Patent Reference 1). HexNAc includes β-N-acetylgalactosamine (GalNAcβ) and β-N-acetylglucosamine (GlcNAcβ), which are indistinguishable by mass spectorometric analysis since they have the same molecular weight. In addition, PSA secreted from LNCaP cells described in Non-Patent Reference 1 was considered not to reflect biological PSA of the prostate cancer patient due to the fact that the sugar chain lacks sialic acid residues. Accordingly, in the present specification, it is possible for the first time to identify β-N-acetylgalactosamine residues and fucose α(1,2) galactose residues at the non-reducing terminal in the serum PSA of a prostate cancer patient by using the TJA-II column, the WFA column or the UEA-I column.

It is considered that the change of the sugar chain structure of PSA with canceration, i.e., appearance of a fucose α(1,2) galactose residue, a β-N-acetylgalactosamine residue and a sialic acid α(2,6) β-N-acetylgalactosamine residue has a background of the changes of glycosyltransferase activities, which are associated with the sugar chain synthesis by the onset of the prostate cancer.

In addition, as described in Patent Reference 1 and Non-Patent Reference 2, in a case where MAA that specifically recognizes Siaα2-3Galβ1-4GlcNAc residues is used to detect the change of the sugar chain structure in the prostate cancer, a part of the blood PSA exists as PSA-ACT, wherein the PSA is bound to serum α1-antichymotrypsin. Since MAA also binds to α1-antichymotrypsin, PSA-ACT bound to an MAA column, although the PSA does not contain Siaα2-3Galβ1-4GlcNAc residues. Accordingly, if MAA is used in the separation of PSA, it is necessary to measure free PSA.

On the other hand, TJA-II that may be used in the present invention recognizes fucose α(1,2) galactose residues and/or β-N-acetylgalactosamine residues existing at the non-reducing terminal of the PSA sugar chain, and WFA recognizes β-N-acetylgalactosamine residues existing at the non-reducing terminal of the PSA sugar chain. However, these sugar chain structures are not linked to serum α1-antichymotrypsin, and therefore, they can be quantified using a total PSA measurement kit. The amount of free PSA is generally equal to or less than 20% of the amount of total PSA, and a total PSA measurement kit may be used in the analysis method of the present invention. Therefore, the present invention is more sensitive than the inventions described in Non-Patent Reference 2 and Patent Reference 1.

[4] Method for Determining Prostate Cancer by the Analysis of Glycosyltransferases As shown in Example 5 described below, the increase of the expression level of a fucosyltransferase, i.e., fucosyltransferase 1 (FUT1) in the prostate cancer is strongly involved in the increase of fucose α(1,2) galactose residues (Fucα1→2Galβ1→R) in PSA of a prostate cancer patient. In addition, it is considered that the increase of β-N-acetylgalactosamine residues (GalNAcβ1→R) and sialic acid α(2,6) β-N-acetylgalactosamine residues (Siaα2→6GalNAcβ1→R) in PSA of a prostate cancer patient is due to increasing the expression level of a β-N-acetylgalactosaminyltransferase, i.e., β-N-acetylgalactosaminyltransferase 4 (β4GALNT4) in the prostate cancer. Accordingly, it is possible to distinguish prostate cancer patients from normal men or prostatic hypertrophy patients by analyzing at least one glycosyltransferase selected from FUT1 and β4GALNT4 in a sample from a cancer patient. The method for determining the prostate cancer of the present invention will be explained below with FUT1 and β4GALNT4, respectively.

In the detection method of the present invention, a method of analyzing FUT1 or β4GALNT4 is not particularly limited as long as the method allows detection of FUT1 or β4GALNT4 quantitatively or semi-quantitatively, or the method allows determination of the presence or absence of FUT1 or β4GALNT4. Examples of the method of analyzing FUT1 or β4GALNT4 include molecular biological assays of measuring mRNA amount of FUT1 or β4GALNT4 (for example, the southern blot method, the northern blot method, and PCR method), immunological techniques using antibody for FUT1 or β4GALNT4 or a fragment thereof (for example, enzyme immunoassay, latex agglutination immunoassay, chemiluminescent immunoassay, fluorescent antibody method, radioimmunoassay, immunoprecipitation method, immunohistological staining method, or the western blot), and biochemical techniques (for example, enzymological assay).

Molecular Biological Assay

The molecular biological assay for FUT1 or β4GALNT4 is not particularly limited as long as it is an assay using primers and probes that can hybridize to genes such as mRNA or cDNA obtained therefrom, and nucleotide thereof in a sample on the basis of the principle of hybridization. For example, the molecular biological assay for FUT1 or β4GALNT4 includes the southern blot method, the northern blot method, and PCR method. However, the molecular biological assay is a particularly preferably real-time PCR method since it is accurate and convenient.

Examples of the real time PCR method include the intercalator method in which a primer set composed of a forward primer and a reverse primer is used, and an intercalator such as SYBR Green I, which is a compound producing fluorescence by binding to a double strand DNA, is added to the PCR reaction system, and the TaqMan method in which the primer set, and a probe of which the 5' terminal is modified with a reporter pigment and the 3' terminal is modified with a quencher pigment (TaqMan probe), are added to the PCR reaction system. Such real-time PCR method itself is well known, and kits and apparatus therefor are also commercially available, and thus the real time PCR method can be easily conducted using commercially available kits and apparatus if the primer set, or the primer set and the probe are synthesized.

The forward primer and the reverse primer, and the probe can be synthesized on the basis of the base sequences of the nucleotides that encode FUT1 or β4GALNT4. Specifically, the forward primer and reverse primer, and the probe for FUT1 can be synthesized by selecting appropriate base sequences from the base sequences (GenBank accession no. NM_000148) of cDNA that encodes FUT1 represented by SEQ ID NO: 1. For example, the base sequence for the forward primer is 5'-AACGCCTCCTCTTCCTGTC-3' (SEQ ID NO: 3) and the base sequence for the reverse primer is 5'-TGGGGTAGACAGTCCAGGTG-3' (SEQ ID NO: 4). In addition, the forward primer and reverse primer, and the probe for β4GALNT4 can be synthesized by selecting appropriate base sequences from the base sequences (GenBank accession no. NM_178537) of cDNA that encodes β4GALNT4 represented by SEQ ID NO: 2. For example, the base sequence for the forward primer is 5'-ACTGG-GAGCTCCTGGACA-3' (SEQ ID NO: 11) and the base sequence for the reverse primer is 5'-TGGTGATAGAAAT-TCCGCAGT-3' (SEQ ID NO: 12).

The length of the primer is not particularly limited, but preferably 15-mer to 35-mer, more preferably 16-mer to 30-mer, and most preferably 19-mer to 25-mer. The length of the probe is not necessarily limited, but preferably 12-mer to 30-mer, more preferably 13-mer to 29-mer, and most preferably 14-mer to 18-mer.

The PCR method, particularly the real time PCR method may include:
(1) a process of purifying mRNA from a sample derived from the human body,
(2) a process of synthesizing cDNA by a reverse transcription enzyme with the purified mRNA as a template,
(3) a process of amplifying DNA using a primer set, or a primer set and a probe, and
(4) a process of detecting the amplified DNA.

It is possible to determine whether a patient suspected of the prostate cancer has the prostate cancer or not by measuring the expression level of mRNA of FUT1 in a sample derived from the body of the patient, and comparing the expression level with the expression level of FUT1 in a sample derived from the body of a normal healthy subject. More specifically, if the expression level of FUT1 of the suspected patient is significantly more than the expression level of FUT1 of the normal healthy subject, it is possible to determine that the patient has the prostate cancer. In addition, the determination of the prostate cancer is possible also by comparing the expression level of β4GALNT4 between prostate cancer patients and normal healthy subjects in the same manner.

For example, in the case of the real time PCR in Examples described below, the average value of FUT1 or β4GALNT4 in normal healthy subjects is calculated, and then the standard deviation (SD) is calculated. The cutoff value for detecting prostate cancer patients is not limited as long as it is a value that allows detection of the prostate cancer. For example, a sample having a value higher than the average value may be determined as positive, or the average value±SD, average value±2SD, or average value±3SD may be also taken as the cutoff value.

Immunological Assay

In a case where an immunological assay is used as the method for the analysis of FUT1, a monoclonal antibody or a polyclonal antibody binding to FUT1 may be used. In addition, in a case where an immunological assay is used as the method for the analysis of β4GALNT4, a monoclonal antibody or a polyclonal antibody binding to β4GALNT4 may be used.

The monoclonal antibody or the polyclonal antibody can be prepared by a known method except that FUT1 or β4GALNT4 is used as an immunizing antigen. For example, the monoclonal antibody can be prepared according to Koehler and Milstein's method (Nature 256: 495-497, 1975). In addition, the polyclonal antibody can be prepared by conventional immunization with an antigen that is FUT1 or β4GALNT4 alone or conjugated to BSA, KLH and the like, which is mixed with an adjuvant such as simple adjuvant or Freund's complete adjuvant, for example, in the skin of a rabbit. The blood is collected at the time when the antibody titer increases, and may be used as it is as an antiserum, or the antibody may be used after purification by a known method.

In a case where an enzyme immunoassay, particularly the sandwich assay is used as the immunological assay, it may be performed as described below. As an example, a case will be explained where an antibody for β4GALNT4 is used.

Antibody binding to β4GALNT4 (capture antibody or first antibody) is immobilized onto an insoluble carrier such as a microtiter plate and bead. Then, blocking of the insoluble carrier is performed with an appropriate blocking agent (for example, bovine serum albumin or gelatin) in order to prevent non-specific binding onto the capture antibody or the insoluble carrier. To the microtiter plate and bead onto which the capture antibody is immobilized, a sample to be tested containing β4GALNT4 is added together with a first reaction solution, to bring the capture antibody into contact with β4GALNT4 for binding (first reaction process). Then, antigens and foreign substances that are not bound to the capture antibody are washed with an appropriate washing solution (for example, a phosphate buffer containing a surfactant). Next, a labeled antibody (second antibody), in which an antibody binding to the captured β4GALNT4 is bound to an enzyme such as horseradish peroxidase (HRP), is added, to bind the labeled antibody to the captured antigen (second reaction process). By this reaction, an immune complex of the capture antibody, β4GALNT4 and labeled antibody is formed on the carrier. The unbound labeled antibody is washed with a washing solution, and a chromogenic substrate and a luminescent substrate for the enzyme of the labeled antibody are added to the immune complex, and following the detection of the signal. In addition, it is also possible to detect a signal by labeling an antibody binding to the second antibody without directly labeling the second antibody.

Examples of the enzyme that labels the antibody include horseradish peroxidase (HRP), alkaline phosphatase, β-galactosidase, and luciferase. Furthermore, in addition to the enzyme, luminescent substances such as acridinium derivatives, fluorescent substances such as europium, radioactive substances such as $I^{125}$, and the like may be used as a label substance. In addition, the substrate and the luminescent inducer may be properly selected in accordance with the label substance. Furthermore, the labeled antibody in the present invention may also include an antibody which bound to a substance such as hapten or low molecular weight peptide as a detection marker, or lectin that may be used in the signal detection of the antigen-antibody reaction.

Furthermore, in a case where a prostatic biopsy sample is used as a sample to be tested, it is possible to determine whether the sample is dignosed as the prostate cancer or not by checking expression of FUT1 or β4GALNT4 at the prostatic gland by immunohistological staining method using monoclonal antibody or polyclonal antibody.

In addition, in a case where blood or the like is used as a sample to be tested, it is possible to determine whether a patient suspected of the prostate cancer has the prostate cancer or not by collecting the blood from the patient suspected of the prostate cancer, whose blood is used as the whole blood itself, or as serum or plasma, measuring the amount of FUT1 or β4GALNT4 in the blood, and comparing that with the amount of FUT1 or β4GALNT4 in the blood or the like collected from normal healthy subjects. More specifically, if the amount of FUT1 or β4GALNT4 of the patient is significantly higher than the amount of FUT1 or β4GALNT4 of normal healthy subjects, it can be determined that the patient has the prostate cancer.

For example, in a case of the sandwich ELISA assay, the average value of FUT1 or β4GALNT4 in normal healthy subjects was calculated, and then the standard deviation (SD) was calculated. The cutoff value for detecting prostate cancer patients is not limited as long as it is a value that allows detection of the prostate cancer. For example, a sample having a value higher than the average value may be determined as positive, or the average value±SD, average value±2SD, or average value±3SD may be taken as the cutoff value.

Biochemical Assay

In a case where an enzymological assay is used as an assay for FUT1 or β4GALNT4, the amount of FUT1 or β4GALNT4 can be analyzed by measuring enzyme activity of FUT1 or β4GALNT4, for example, according to the method of Larsen, et al. [Larsen R D, Ernst L K, Nair R P, Lowe J B. Proc. Natl Acad Sci USA, 87, 6674-6678 (1990)], or Gotoh, et al. [Gotoh M, Sato T, Kiyohara K, Kameyama A, Kikuchi N, Kwon Y D, Ishizuka Y, Iwai T, Nakanishi H, Narimatsu H. FEBS Lett., 562, 134-140 (2004)].

Examples of the sample used in the analysis of FUT1 or β4GALNT4 in the method for detecting prostate cancer by the analysis of glycosyltransferase of the present invention, include biological samples and samples derived from the human body possibly containing FUT1 or β4GALNT4. Specific examples of the sample to be tested include body fluid samples such as urine, blood, serum, plasma, spinal fluid and saliva, cell, tissue, organ, and preparations thereof (for example, a biopsy sample, particularly a prostatic biopsy sample). The sample to be tested is preferably blood, serum, plasma, or a prostatic biopsy sample, particularly preferably blood, serum, or plasma (hereinafter, sometimes referred to as a blood or the like). Blood, serum or plasma is appropriate as samples to be tested for detecting the prostate cancer, because little FUT1 or β4GALNT4 exists in the tissue, blood, serum or plasma of normal healthy subjects or prostatic hypertrophy patients.

[5] Detection Kit for the Prostate Cancer by the Analysis of Glycosyltransferase The kit for detecting the prostate cancer by molecular biological analysis of the present invention may contain a primer set, or a primer set and a probe that hybridize specifically to nucleotides that encode FUT1 or β4GALNT4. In the detection kit of the present invention, a forward primer, a reverse primer, and a probe may be contained as a mixture, or may be contained as separated reagents. In addition, the kit of the present invention may further contain reagents and/or enzymes that are necessary in performing the real time PCR method, in addition to the primers and the probe. Furthermore, the kit of the present invention may contain a manual that states the use for detection or measurement of the prostate cancer, or the use for distinction of the prostate cancer from normal healthy subjects or prostatic hypertrophy. In addition, these descriptions may be also attached to the container.

The kit for detecting the prostate cancer by immunological analysis of the present invention may contain an antibody that specifically binds to FUT1 or β4GALNT4 or a fragment thereof in a desired form depending on the immunological technique to be used. As the antibody, a monoclonal antibody or a polyclonal antibody may be used. The antibody fragment is not particularly limited as long as it has the ability to specifically bind to FUT1 or β4GALNT4, examples include, for example, Fab, Fab', F(ab')$_2$, or Fv.

For example, in a case where an immunological technique using a labeled antibody is used, such as enzyme immunoassay detected by fluorescence, chemiluminescence, or radioactivity, the diagnosis kit may contain the antibody or a fragment thereof in the form of a labeled antibody or a labeled antibody fragment conjugated with a label substance. Concrete examples of the label substance include enzymes such as peroxidase, alkaline phosphatase, β-D-galactosidase or glucose oxidase, fluorescent substances such as fluorescein isothiocyanate or rare-earth metal chelate, radioactive isotopes such as $^3$H, $^{14}$C or $^{125}$I, and miscellaneously, biotin, avidin, and chemiluminescent substances. In a case where the enzyme or the chemiluminescent substance is used, the kit preferably contains an appropriately selected substrate and the like since the enzyme or the chemiluminescent substance cannot generate measurable signals by themselves.

Furthermore, the kit of the present invention may contain a manual that states the use for detection or measurement of the prostate cancer, or the use for distinction of the prostate cancer from normal healthy subjects or prostatic hypertrophy. In addition, these descriptions may be also attached to the container.

EXAMPLES

The present invention now will be further illustrated by, but is by no means limited to, the following Examples and Comparative Examples.

Example of TJA-II Purification

TJA-II was purified from 20 g of the tuberous root of *Trichosanthes japonica* as previously reported (Yamashita et al., J. Biol. Chem., 267, 25441-25422, 1992). Specifically, the tuberous root of *Trichosanthes japonica* was finely shredded, and homogenized with 16 mL of 10 mM phosphate buffer (pH 7.4) containing 0.15 M NaCl using a Waring blender. The resultant liquid was centrifuged at 1000 g for 30 minutes, and 35% to 55% saturated ammonium sulfate fraction precipitate of the obtained supernatant was dissolved in water, and dialyzed with distilled water. After lyophilization, 435 mg of the 35% to 55% saturated ammonium sulfate precipitate was dissolved in 6 mL PBS, and was applied to a 10 mL of porcine stomach mucin-Sepharose 4B (10 mg/mL gel) column that was equilibrated with PBS. The column was washed, and then eluted with PBS containing 0.1 M lactose, to obtain TJA-II.

Example of Column Preparation

The TJA-II column and the WFA column were prepared by coupling purified TJA-II and WFA (manufactured by EY Laboratory) respectively to sepharose columns. Specifically, the TJA-II column was prepared using CNBr-Sepharose 4B (manufactured by GE HealthCare) by binding TJA-II to the column in the density of 3 mg per 1 mL gel volume according to the enclosed protocol recommended by the manufacturer.

In addition, the WFA column was prepared using WFA (manufactured by EY Laboratory) and CNBr-Sepharose 4B (manufactured by GE HealthCare) in the same manner.

Example 1

Analysis of PSA Using TJA-II

In this example, the amount of PSA was measured by the method for analyzing PSA of the present invention using the TJA-II column prepared in the example of column preparation, for 15 patients diagnosed as having prostate cancer and 9 patients diagnosed as having prostatic hypertrophy and having 4.0 ng/mL or more of total PSA.

The TJA-II column (1 mL volume) was equilibrated with a phosphate buffer containing 0.1% bovine serum albumin (BSA) at 4° C. 1 µL to 50 µL of the serum sample was diluted with a phosphate buffer to the volume of 200 µL, applied to the column, and held for 30 minutes. Then, the column was washed with 5-fold volume of a washing buffer (phosphate buffer containing 0.1% BSA), and fractionated to 1 mL for each, to obtain the TJA-II non-bound molecules. The column was stood at room temperature, and then fractionated to 1 mL for each and eluted with 5-fold volume of an eluting buffer (phosphate buffer containing 10 mM lactose and 0.1% BSA), to obtain the TJA-II bound molecules. The total amount of PSA was measured using Access Hybritech total PSA (manufactured by Beckman Coulter, Inc.) for the serum sample before a separation by the TJA-II column, the TJA-II non-bound molecules, and the TJA-II bound molecules. The recovery rate of PSA from the TJA-II column was 97% to 100% at any time. The amount of PSA before a separation in the serum sample, the amount of PSA in the TJA-II binding fraction, and TJA-II binding rate of PSA are shown in Table 1. Meanwhile, the TJA-II binding rate was calculated by the following equation.

TJA-II binding rate=(amount of PSA in the TJA-II binding fraction/total amount of PSA in the TJA-II non-binding fraction and in the TJA-II binding fraction)×100%

In addition, the free PSA in the serum sample before a separation was measured using Access Hybritech free PSA (manufactured by Beckman Coulter Inc.). From the amount of total PSA and the amount of free PSA, the ratio of free PSA/total PSA was calculated. The results are shown in Table 1, FIG. 2 and FIG. 3. Meanwhile, the age, the clinical stage and the Gleason score of the cancer patients are shown in Table 2. The clinical stage indicates the progress level of the prostate cancer. In addition, the Gleason score indicates the degree of malignancy of the prostate cancer in 5 steps of the pathological classes. "1" means mildest cancer, and "5" means worst cancer. In many cases, the prostate cancer has different tissues of different degrees of malignancy, and thus the most prevalent tissue and the next most prevalent tissue are added to obtain the score, which is the Gleason score. For example, if the most prevalent tissue is "3" and the next most prevalent tissue is "4", the Gleason score is "3"+"4"="7". When the Gleason score is "6" or less, the cancer is considered to be low-grade cancer in malignancy, "7" to be intermediate-grade cancer in malignancy, and "8" to "10" to be high-grade cancer in malignancy.

TABLE 1

| Sample | | PSA in serum sample (ng/mL) | TJA-II-bound PSA in serum sample (ng/mL) | TJA-II-unbound PSA in serum sample (ng/mL) | TJA-II binding ratio (%) | Free PSA/ total PSA |
|---|---|---|---|---|---|---|
| Prostatic hypertrophy | 1 | 17.00 | 0.20 | 16.3 | 1.2 | 19.0 |
| | 2 | 10.40 | <0.005 | 10.1 | <0.05 | 5.0 |
| | 3 | 10.20 | 0.02 | 9.87 | 0.2 | 79.0 |
| | 4 | 6.80 | 0.04 | 6.56 | 0.6 | 76.0 |
| | 5 | 8.30 | 0.12 | 7.93 | 1.5 | 22.0 |
| | 6 | 9.60 | 0.17 | 9.14 | 1.8 | 7.0 |
| | 7 | 8.00 | <0.005 | 7.75 | <0.05 | 6.0 |
| | 8 | 9.20 | 0.09 | 8.83 | 1.0 | 16.0 |
| | 9 | 8.20 | <0.005 | 7.95 | <0.05 | 12.0 |
| Prostate cancer | 1 | 892.20 | 128.00 | 808.30 | 6.4 | 4.5 |
| | 2 | 101.00 | 6.60 | 92.92 | 5.0 | 11.9 |
| | 3 | 69.90 | 2.40 | 65.70 | 3.0 | 4.9 |
| | 4 | 944.80 | 9.50 | 873.95 | 4.5 | 16.8 |
| | 5 | 180.00 | 6.30 | 162.00 | 7.0 | 7.8 |
| | 6 | 3597.00 | 388.50 | 3100.60 | 10.8 | 3.9 |
| | 7 | 68.00 | 5.58 | 60.38 | 8.2 | 13.0 |
| | 8 | 4.30 | 0.90 | 3.27 | 21.0 | NT |
| | 9 | 6.00 | 0.84 | 4.98 | 14.0 | NT |
| | 10 | 10.00 | 0.46 | 9.24 | 4.6 | NT |
| | 11 | 4.50 | 1.04 | 3.32 | 23.0 | NT |
| | 12 | 53.80 | 4.30 | 47.88 | 8.0 | 17.0 |
| | 13 | 4.70 | 0.24 | 4.32 | 5.0 | 13.5 |
| | 14 | 21.20 | 0.85 | 19.71 | 4.0 | 10.0 |
| | 15 | 12.10 | 0.61 | 11.13 | 5.0 | 10.0 |

TABLE 2

| Sample | | Age | Clinical stage | Gleason score |
|---|---|---|---|---|
| Prostatic hypertrophy | 1 | 74 | — | — |
| | 2 | 75 | — | — |
| | 3 | 65 | — | — |
| | 4 | 70 | — | — |
| | 5 | 65 | — | — |
| | 6 | 51 | — | — |
| | 7 | 71 | — | — |
| | 8 | 71 | — | — |
| | 9 | 52 | — | — |
| Prostate cancer | 1 | 83 | 3c | 7 |
| | 2 | 77 | 3b | 9 |
| | 3 | 66 | 3b | 9 |
| | 4 | 64 | 3b | 9 |
| | 5 | 81 | 4 | 9 |
| | 6 | 81 | 3c | 7 |
| | 7 | 83 | 3b | 9 |
| | 8 | unknown | ND | ND |
| | 9 | unknown | ND | ND |
| | 10 | unknown | ND | ND |
| | 11 | unknown | ND | ND |
| | 12 | 74 | 3b | 9 |
| | 13 | 59 | 1c | 7 |
| | 14 | 64 | 1c | 7 |
| | 15 | 64 | 2a | 9 |

Figure 2:
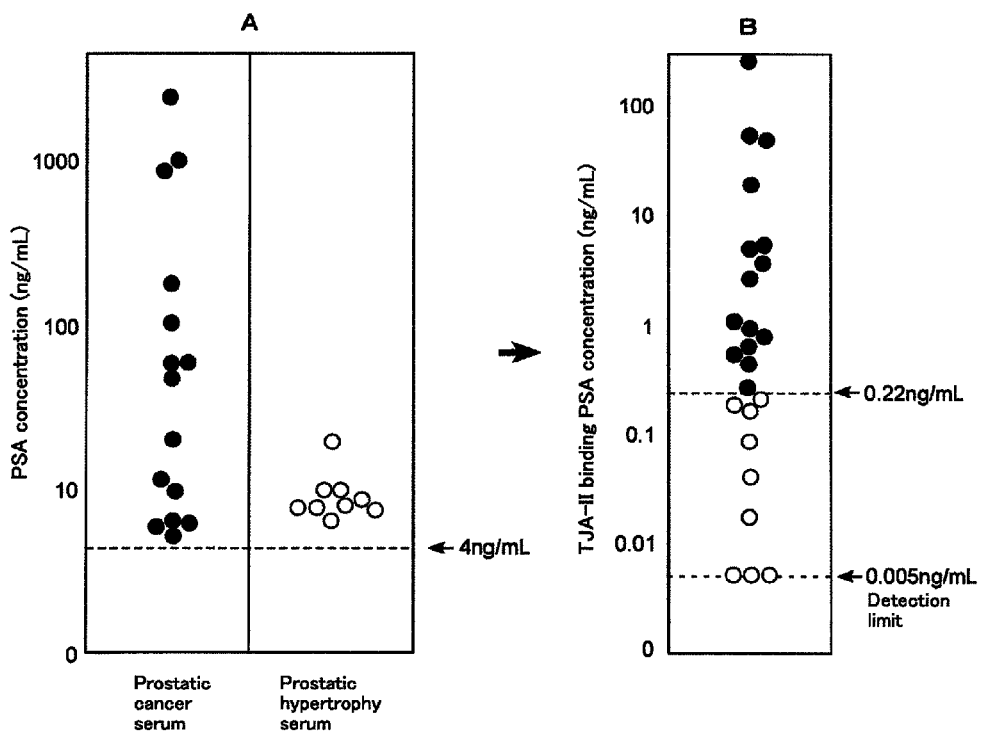
FIG. 2 is a graph showing a quantity of PSA in a serum before the fractionation using a TJA-II column (A) and a quantity of PSA in the TJA-II-bound fractions (B) of a prostate cancer patient and a prostatic hypertrophy patient. A black circle (•) shows a prostate cancer patient. A white circle (○) shows a prostatic hypertrophy patient.
Figure 3:
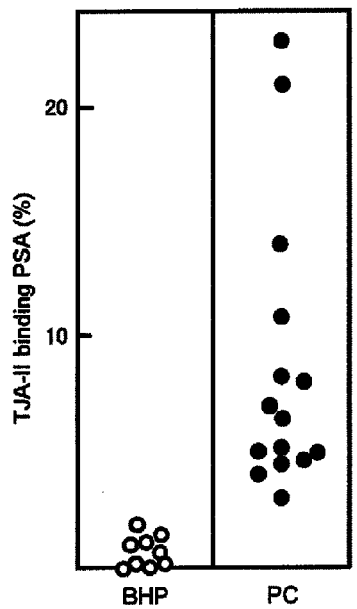
FIG. 3 is a graph showing a TJA-II binding rate of the PSA from a prostate cancer patient serum (PC: •) and the PSA from a prostatic hypertrophy patient serum (BHP: ○).

As shown in FIG. 2 and FIG. 3, neither the amounts of TJA-II-bound PSA, nor the binding rates for TJA-II overlapped between the prostate cancer patients and the prostatic hypertrophy patients, which indicated that the prostate cancer patients can be distinguished from the prostatic hypertrophy patients. If the cutoff value of the TJA-II-bound PSA is assumed to be 250 pg/mL, and the cutoff value of the TJA-II binding rate tentatively to be 2%, the prostatic hypertrophy patients can be distinguished from the prostate cancer patients with 100% accuracy. In various clinical stages and Gleason scores, no significant difference was found in the TJA-II binding rate and the amount of TJA-II-bound PSA.

Example 2

In this example, the amount of PSA was measured by the method for analyzing PSA of the present invention for 3 patients diagnosed as having the prostate cancer using the WFA column prepared in the example of column preparation.

Specifically, the procedures of Example 1 were repeated except that the WFA column and an eluting buffer (phosphate buffer containing 10 mM GalNAc and 0.1% BSA) were used instead of the TJA-II column and the eluting solution (phosphate buffer containing 10 mM lactose and 0.1% BSA), and the serum samples of the 3 prostate cancer patients were analyzed, to obtain the amount of WFA-bound PSA and the WFA binding rate. The results of the WFA binding rate are shown in Table 3.

Meanwhile, the WFA binding rate was calculated by the following equation.

WFA binding rate=(amount of PSA in the WFA binding fraction/total amount of PSA in the WFA non-binding fraction and in the WFA binding fraction)×100%

In addition, the TJA-II binding rates are shown in Table 3 for comparison.

TABLE 3

| Sample | | PSA in serum sample (ng/mL) | WFA-bound PSA in serum sample (ng/mL) | WFA-unbound PSA in serum sample (ng/mL) | WFA binding ratio (%) | TJA-II binding ratio (%) |
|---|---|---|---|---|---|---|
| Prostate cancer | 6 | 3597.00 | 327.98 | 3161.11 | 9.4 | 10.8 |
| | 12 | 53.80 | 3.91 | 48.27 | 7.5 | 8.0 |
| | 15 | 12.10 | 0.49 | 11.50 | 4.2 | 5.0 |

The PSA recovery rate from the WFA column was 90% to 98%. In addition, the WFA binding rate was nearly correlated to the TJA-II binding rate, and WFA is bound to PSA having β-N-acetylgalactosamine residues, which makes it possible to separate PSA of the prostate cancer patient.

However, the WFA binding rate was from 4.2% to 9.4%, which was somewhat lower than the TJA-II binding rate. This suggests the possibility that PSA having an affinity only for TJA-II exists in the blood of the prostate cancer patient. In other words, this suggests the possibility that PSA having only fucose α(1,2) galactose residues (Fucα1→2Galβ1→R) but having no β-N-acetylgalactosamine residues (GalNAcβ1→R) exists.

Example 3

In this example, it was found that binding of PSA to the TJA-II column increased by treating the serum of the prostate cancer patient with sialidase.

The procedures of Example 1 were repeated except that 20 samples were used from the serum of patients diagnosed as having prostate cancer and 20 samples were used from the serum of patients diagnosed as having prostatic hypertrophy, to measure the TJA-II binding rates of PSA. The results are shown in FIG. 5A. The TJA-II binding rate in prostate cancer was about 2% or more, whereas the TJA-II binding rate in prostatic hypertrophy was less than about 2%.

Next, the sialidase treatment was performed using 5 samples from the sera of the patients diagnosed as having the prostate cancer and 5 samples from the sera of the patients diagnosed as having the prostatic hypertrophy. Specifically, 1 µL to 50 µL of the serum sample was diluted with a phosphate buffer containing 0.1% BSA to the volume of 200 µL. To the obtained diluted sample, 50 mU sialidase derived from *Arthrobacter ureafaciens* was added, and the mixture was reacted at 37° C. for 1 hour. The procedures of Example 1 were repeated except that the resulting sialidase-treated samples were used. The results are shown in FIG. 5B.

Figure 5:
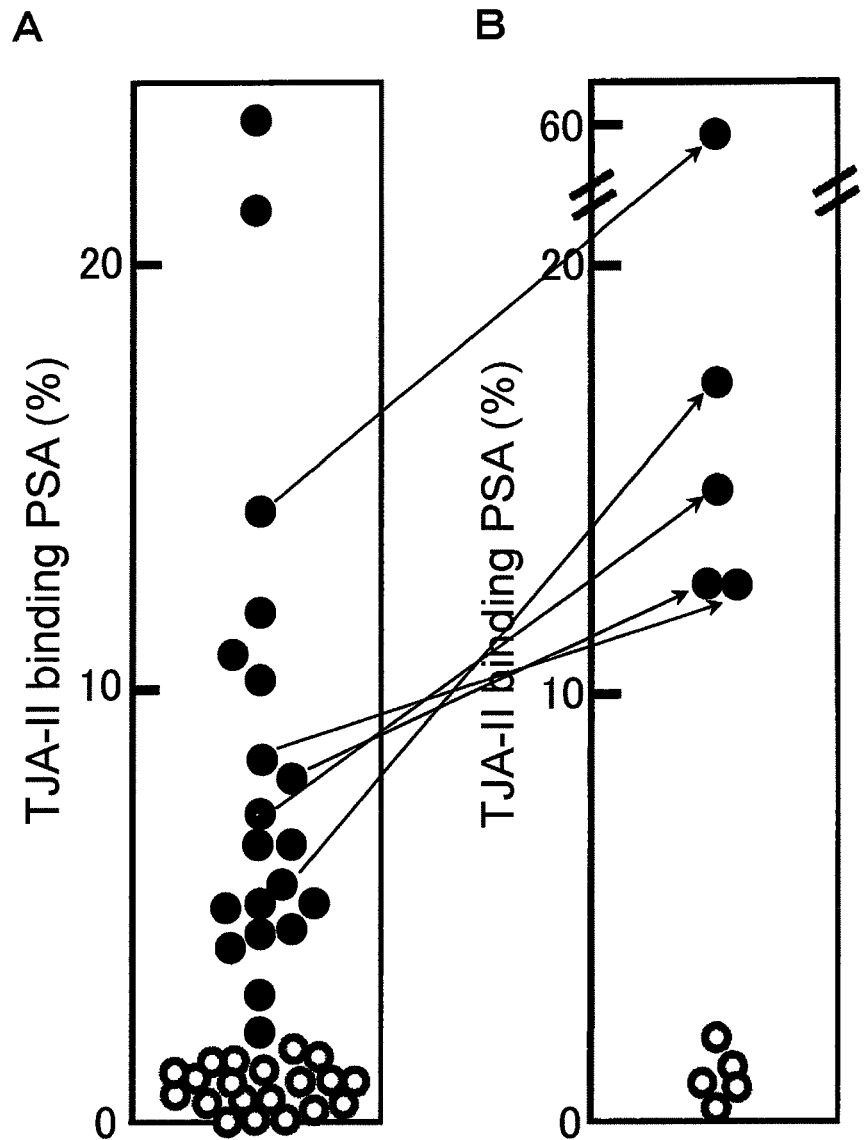
FIG. 5 is a graph showing TJA-II binding rates of PSA in serum of prostate cancer patients and prostatic hypertrophy patients before sialidase treatment (A) and after sialidase treatment (B). A black circle (•) shows a prostate cancer patient. A white circle (○) shows a prostatic hypertrophy patient.

The arrow in FIG. 5 shows that the TJA-II binding rate of PSA is increased by the sialidase treatment in the five sera of the patients diagnosed as having the prostate cancer. On the other hand, no increase of the TJA-II binding rate of PSA was found in the sera of the patients diagnosed as having the prostatic hypertrophy.

Furthermore, similar procedures were repeated using sialidase derived from *Salmonella typhimurium* and specific to sialic acid α(2,3). However, the TJA-II binding rate of PSA was not increased with sialidase derived from *Salmonella typhimurium* even in the sera of the patients diagnosed as having the prostate cancer.

These results show the following. The sialidase derived from *Arthrobacter ureafaciens* mainly cleaves the α(2,6) and α(2,3) bindings of sialic acid. On the other hand, the sialidase derived from *Salmonella typhimurium* cleaves α(2,3) binding of sialic acid. That is, it is considered that the sialic acid of PSA in the serum of the prostate cancer patient, is bound to the sialic acid α(2,6) β-N-acetylgalactosamine residue, not sialic acid α(2,3) β-N-acetylgalactosamine residue (FIG. 6).

Example 4

In this example, the binding rates of PSA to the TJA-II column, the UEA-I column and the WFA column were examined for PSA in the sera of the prostatic hypertrophy patients, PSA in the sera of the prostate cancer patients, and PSA in the seminal fluids of the normal men. For the binding rate to the TJA-II column, the binding rates were examined for sialidase-treated samples, and for non-sialidase-treated samples.

Measurement of the binding rate to the TJA-II column was performed in accordance with the method described in Example 1. Measurement of the binding rate to the WFA column was performed in accordance with the procedures described in Example 2. Measurement of the binding rate to the TJA-II column of the sialidase-treated samples was performed in accordance with the procedures described in Example 3.

In addition, measurement of the binding rate to the UEA-I column was performed as described below. The amount of UEA-I-bound PSA was measured using agarose immobilized with Ulex europaeus agglutinin-1 (UEA-I) (UEA-I agarose: J-oil mills). Specifically, the procedures of Example 1 were repeated except that UEA-I agarose and an eluting buffer (phosphate buffer containing 50 mM fucose and 0.1% BSA) were used instead of the TJA-II column and the eluting solution (phosphate buffer containing 10 mM lactose and 0.1% BSA), to measure the UEA-I binding rate. The results are shown in Table 4.

TABLE 4

| Lectin | Recognized sugar chain | PSA in serum of prostatic hypertrophy patient | PSA in serum of prostate cancer patient | PSA in seminal fluid |
|---|---|---|---|---|
| TJA-II | Fucα1→2Galβ1→4 (3) GlcNAc | 2.0% | 16% | 2% |
| TJA-II (Sialdase treatment) | and GalNAcβ1→ | 2.0% | 59% | 8.4% |
| UEA-I | Fucα1→2Galβ1→4GlcNAc | <1% | 5% | <1% |
| WFA | GalNAcβ1→ | <1% | 11% | <1% |

Little PSA in the serum of the prostatic hypertrophy patients is bound to the TJA-II column, the UEA-I column or the WFA column. On the other hand, for PSA in the sera of the prostate cancer patients, 16% PSA is bound to the TJA-II column, 5% PSA is bound to the UEA-I column, and 11% PSA is bound to the WFA column. These data show that PSA in the sera of the prostate cancer patients has β-N-acetylgalactosamine residues and fucose α(1,2) galactose residues at the non-reducing terminal.

Furthermore, the binding rate to the TJA-II column increased from 11% to 59% by treating PSA in the sera of the prostate cancer patients with sialidase derived from *Arthrobacter ureafaciens*. These results showed that PSA in the sera of the prostate cancer patients has sialic acid α(2,6) β-N-acetylgalactosamine residues.

Comparative Example 1

In this Comparative Example, separation and measurement of PSA of prostate cancer patients were performed using MAA column, which is the lectin described in Patent Reference 1.

Purification of MAA was performed in accordance with the method previously reported (Kawaguchi et al., J. Biol. Chem., 249, 2786-2792, 1974). Concretely, 50 g of seeds of Maackia amurensis was homogenized finely with several hundred mL PBS by a homogenizer, stirred overnight, and then centrifuged at 9000 rpm for 30 minutes to exclude the precipitate. 50 to 80% ammonium sulfate fraction of this extract solution (210 mL) was dialyzed with PBS, and centrifuged to exclude the precipitate. Then, a portion (30 mL) of the resultant was added to thyroglobulin-Sepharose (19 mg/mL, 15 mL), washed with PBS, and then eluted with 0.15 M glycine hydrochloride buffer (pH 2.5) containing 0.1 M lactose and 0.075 M NaCl. Portions having high lectin activity were pooled, concentrated, and then dialyzed with 50 mM phosphate buffer (pH 4.5) for substitution. The precipitate was removed with the centrifuge procedure, and then the resultant was added to SP-Sephadex C-50 (100 mL) that was equilibrated with 50 mM phosphate buffer (pH 4.5), and the non-adsorbed fractions were collected and concentrated, to obtain purified MAA.

The MAA-Sepharose column was prepared using the purified MAA. The MAA column was prepared using CNBr-Sepharose (manufactured by GE HealthCare) by binding the MAA to the column in the concentration of 3 mg per 1 mL gel volume according to the enclosed protocol recommended by the manufacturer.

In order to check the binding property for a sialic acid α(2,3) galactose residue of the MAA column, the binding was checked using a oligosaccharide having 3 sialic acid α(2,3) galactose residues. At a temperature of 4° C., the MAA column (1 mL volume) was equilibrated with a phosphate buffer containing 0.1% bovine serum albumin (BSA) and 0.02% Tween. A tri-antennary oligosaccharide having 3 sialic acid α(2,3) galactose residues was applied to the column, and held for 30 minutes. Then, the column was washed with a 5-fold volume of a washing buffer (phosphate buffer containing 0.1% BSA and 0.02% Tween), and fractionated to 1 mL for each to obtain the MAA non-bound molecules. Sequentially, the column was stood at room temperature, and then fractionated to 1 mL for each fraction and eluted with a 5-fold volume of an eluting buffer (phosphate buffer containing 400 mM lactose, 0.1% BSA and 0.02% Tween), to obtain the MAA bound molecules. The oligosaccharide having 3 sialic acid α(2,3) galactose residues was weakly interacted with MAA-Sepharose column and recovered with a washing buffer.

Figure 4:
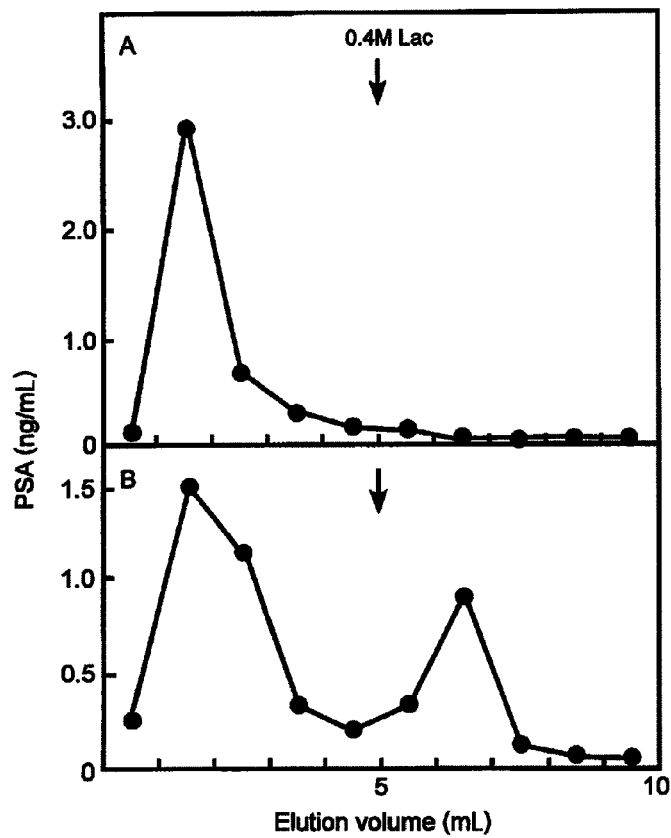
FIG. 4 is a graph showing the results of MAA column chromatography. PSA from normal seminal fluid (A) and PSA from prostate cancer patient serum (B) were fractionated by using an MAA column, followed by measuring an amount of free PSA.

Next, using this MAA column, the binding of PSA of a prostate cancer patient to the MAA column was examined. The MAA column (1 mL volume) was equilibrated with a phosphate buffer containing 0.1% bovine serum albumin (BSA) and 0.02% Tween at 4° C. 10 µL of the serum sample was diluted with the phosphate buffer to the volume of 200 µL, applied to the column, and held for 30 minutes. Then, the column was washed with 5-fold volume of a washing buffer (phosphate buffer containing 0.1% BSA and 0.02% Tween), and fractionated to 1 mL for each fraction to obtain five MAA non-binding fractions. The column was stood at room temperature, and then fractionated to 1 mL for each fraction and eluted with a 5-fold volume of an eluting buffer (phosphate buffer containing 400 mM lactose, 0.1% BSA and 0.02% Tween), to obtain five MAA binding fractions. For each of the fractions, the total PSA amount was measured using Access Hybritech total PSA (manufactured by Beckman Coulter Inc.). For control, the same procedures were repeated using 5 ng of purified PSA from normal seminal fluid, and the total amount of PSA was measured. The results of PSA of the prostate cancer patients are shown in FIG. 4(B), and the results of PSA from normal seminal fluid are shown in FIG. 4(A).

Most of PSA from normal seminal fluid was detected in the second MAA non-binding fraction. However, the total amount of the PSA in all the fractions, was 3.5 ng, relative to 5 ng of normal PSA that was applied to the MAA column. Therefore, the recovery rate was 70%, and 30% was considered to be as bound to the column.

On the other hand, PSA of the prostate cancer patients is divided into the non-bound PSA detected in the second MAA non-binding fraction, the slightly bound PSA detected in the shoulder portion of the third MAA non-binding fraction, and the bound PSA eluted with 400 mM lactose. The total of the PSA amount in all the fractions was 4 ng/mL, relative to 10 ng/mL that was the amount of PSA in the serum sample before a separation. Thus, only about 40% of the amount of PSA before separation was recovered. This recovery rate did not improve even with use of 0.1 M acetic acid solution as the eluting solution. Furthermore, as for the used PSA of the prostate cancer patient, the ratio of free PSA/total PSA was 3.6, and 96.4% PSA existed in the form of PSA-ACT that was bound to α-antichymotrypsin. Since α-antichymotrypsin has one sialic acid α(2,3) galactose residue per one molecule, PSA-ACT was anticipated to be bound to the MAA column. However, much of PSA was detected as the non-adsorbed PSA that was detected in the second MAA non-binding fraction, and as the slightly adsorbed PSA that was detected in the shoulder portion of the third MAA non-binding fraction.

In other words, the result that the oligosaccharide having 3 sialic acid α(2,3) galactose residues is weakly interacted with the MAA column, and the result that some of PSA-ACT is not bound, show that the binding of PSA to the MAA lectin column is weak. In addition, although the binding of PSA to MAA is weak, it was considered that the recovery rate of PSA from MAA column was poor, that elution by the haptenic sugar was imcomplete, and that measurement by MAA with good reproducibility and high accuracy was difficult.

Example 5

In this example, a β-N-acetylgalactosaminyltransferase that adds β-N-acetylgalactosamine residues to PSA, a fucosyltransferase that adds fucose residues, and a sialyltransferase that adds sialic acid residues in the prostate cancer patients were identified, and the expression levels of these glycosyltransferases in the prostate cancer tissue were confirmed.

First of all, mRNA expression levels of fucosyltransferase 1 (FUT1), and fucosyltransferase 2 (FUT2), β-N-acetylgalactosaminyltransferase 2 (β4GALNT2), β-N-acetylgalactosaminyltransferase 3 (β4GALNT3) and β-N-acetylgalactosaminyltransferase 4 (β4GALNT4), and sialyltransferase 1 (hereinafter, referred to as a ST6GAL1) and sialyltransferase 2 (hereinafter, referred to as a ST6GAL2) in human prostate cancer-derived cells and normal human prostatic tissues, were examined by the method of real time polymerase chain reaction (hereinafter, referred to as a real time PCR). As the human prostate cancer-derived cell, DU145 (RCB2143; provided from RIKEN BioResource Center) and PC-3 (JCRB9110; provided from Health Science Research Resources Bank) were used. The total RNA was extracted using ISOGEN (Nippon Gene, Co., Ltd.) from the normal prostatic tissue and the DU145 cells and PC-3 cells, which were preserved using RNA later (Ambion, Inc.), and further extraction was performed with chloroform/isopropyl alcohol. Extracted RNA was precipitated with ethanol, and then dissolved in diethyl carbonate-treated distilled water. The RNA was subjected to reverse transcription reaction with oligo(dT) primer using Superscript III (Invitrogen Corporation), to obtain cDNA. The real time PCR was performed by a Dice (registered trademark) real time system (TP800, Takara Bio Inc.) using Power SYBR (registered trademark) Green PCR master mix (Life Technologies), and primers that were gene-specific to each glycosyltransferase.

The primers of each glycosyltransferase used are as follows.

```
FUT1:
                                        (SEQ ID NO: 3)
5'-AACGCCTCCTCTTCCTGTC-3',
and (SEQ ID NO: 4)
5'-TGGGGTAGACAGTCCAGGTG-3';
(GenBank accession no. NM_000148)

FUT2:
                                        (SEQ ID NO: 5)
5'-CCTCAACATCAAAGGCACTG-3',
and (SEQ ID NO: 6)
5'-GGCCTATTGCATTGATCGTC-3';
(GenBank accession no. NM_000511)

B4GALNT2:
                                        (SEQ ID NO: 7)
5'-GATTTTTCCAACCCCTGGAT-3',
and (SEQ ID NO: 8)
5'-GAAGTTGACCACGCCACTG-3';
(GenBank accession no. NM_153446)

B4GALNT3:
                                        (SEQ ID NO: 9)
5'-AGGTCACGCGAGTCTTCTTG-3',
and (SEQ ID NO: 10)
5'-ACAATGCGCTGTAGCTGGTA-3';
(GenBank accession no. NM_173593)

B4GALNT4:
                                        (SEQ ID NO: 11)
5'-ACTGGGAGCTCCTGGACA-3',
and (SEQ ID NO: 12)
5'-TGGTGATAGAAATTCCGCAGT-3';
(GenBank accession no. NM_178537)

ST6GAL1:
                                        (SEQ ID NO: 13)
5'-TCAGCGGGATCTCTGAAGTC-3',
and (SEQ ID NO: 14)
5'-AAACCTCAGGACTGCGTCA-3';
(GenBank accession no. NM_003033)

ST6GAL2:
                                        (SEQ ID NO: 15)
5'-TCCTTGGGCGAGGAAATAG-3',
and (SEQ ID NO: 16)
5'-CCCAACATCTTTCTCATAACCAC-3'.
(GenBank accession no. NM_006927)
```

Normalization of mRNA expression was performed using GAPDH: 5'-ATCCACATCGCTCAGACAC-3' (SEQ ID NO: 17), and 5'-GCCCAATACGACCAAATCC-3' (SEQ ID NO: 18) (GenBank accession no. NM_002046) as internal standard primers.

The real time PCR program was repeated 40 cycles of 95° C., 10 seconds and 60° C., 40 seconds. A single sharp peak was obtained by respective primer set, and specific PCR product was amplified, and no primer dimer was found. The tests were repeated three times for each of the samples. The results are shown in Table 5.

TABLE 5

| Glycosyl transferase | Normal tissue 1 | Normal tissue 2 | PC3 | DU145 |
|---|---|---|---|---|
| FUT1 | 0.71 | 0.61 | 1.4 | 3.3 |
| FUT2 | <0.5 | <0.5 | 1 | 1.3 |
| B4GALNT2 | <0.005 | <0.05 | <0.005 | 0.01 |
| B4GALNT3 | <0.5 | <0.5 | <0.5 | 2.9 |
| B4GALNT4 | 0.4 | 0.81 | 3.9 | 4 |

TABLE 5-continued

| Glycosyl transferase | Normal tissue 1 | Normal tissue 2 | PC3 | DU145 |
|---|---|---|---|---|
| ST6GAL1 | 0.3 | 1.0 | 0.26 | 0.22 |
| ST6GAL2 | <0.02 | <0.02 | 0.04 | <0.02 |

As is obvious from Table 5, for FUT1 and β4GALNT4, the levels of mRNA expression was remarkably high in the prostate cancer-derived cells compared to normal tissue. In addition, for FUT2, β4GALNT2 and β4GALNT3, the levels of mRNA expression were approximatly the same as GAPDH of the internal standard in the normal tissue, but cells having high expression levels were found in the prostate cancer-derived cells. On the other hand, there was little difference found in the level of ST6GAL1 mRNA between the prostate cancer-derived cells and the normal tissue.

Next, for mRNA of FUT1 and β4GALNT4, expression levels in prostatic normal tissue and cancer tissue were compared. The real time PCR procedures were repeated using the primers of FUT1 and β4GALNT4, and 2 samples of the prostatic normal tissues and 2 samples of the cancer tissue.

Figure 7:
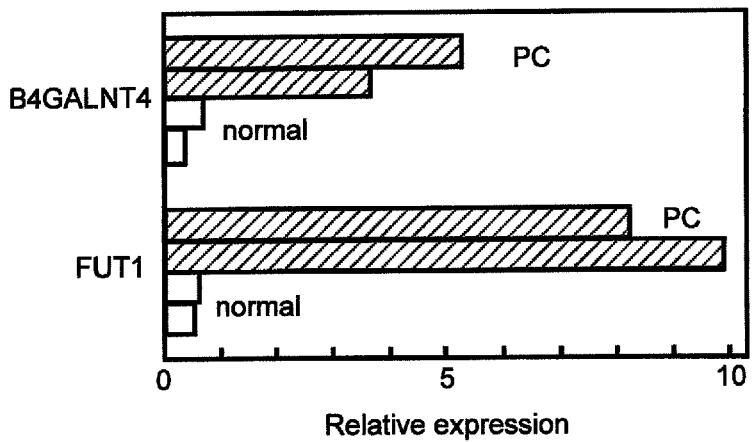
FIG. 7 is a graph showing the expression levels of mRNA for fucosyltransferase 1 (hereinafter, sometimes referred to as FUT1) and $\beta$-N-acetylgalactosaminyltransferase 4 (hereinafter, sometimes referred to as $\beta$4GALNT4) in normal tissues and cancer tissues of postate grand.

The results are shown in FIG. 7.

The levels of mRNA expression of FUT1 and β4GALNT4 increased about 7-fold to 20-fold in the cancer tissue compared to that of the normal tissue. These results suggested that in the PSA of the prostate cancer patient, β4GALNT4 is involved in the increase of 3-N-acetylgalactosamine residues (GalNAcβ→1R) and sialic acid α(2,6) β-N-acetylgalactosamine residues (Siaα2→6GalNAcβ1→R), and FUT1 is involved in the increase of fucose α(1,2) galactose residues (Fucα1→2Galβ1→R).

INDUSTRIAL APPLICABILITY

With the method for analyzing PSA and the analysis kit of PSA of the present invention, it is possible to distinguish definitely between prostate cancer patients and prostatic hypertrophy patients. Accordingly, it is possible to find the prostate cancer in the early stage in a health examination. In addition, because it is possible to distinguish definitely between the prostate cancer and the prostatic hypertrophy, subjects for needing prostatic biopsy for confirmed diagnosis can be reduced, which can reduce the burden of patients.

Although the present invention has been described with reference to specific embodiments, various changes and modifications obvious to those skilled in the art are possible without departing from the scope of the appended claims.

The invention claimed is:

1. A method for determining an amount, if any, of PSA having a β-N-acetylgalactosamine residue and/or a sialic acid α(2,6) β-N-acetylgalactosamine residue in a sample, comprising the following step of
   (a) adding a sialidase to a sample possibly containing PSA, to obtain the sialidase-treated sample;
   (b) determining an amount of PSA having β-N-acetylgalactosamine residue in the sialidase-treated sample by an immunoassay using an antibody specific to PSA and a lectin having an affinity for β-N-acetylgalactosamine residue.

2. The method for determining an amount, if any of PSA having a β-N-acetylgalactosamine residue and/or a sialic acid α(2,6) β-N-acetylgalactosamine residue, comprising the steps of
   (a) adding sialidase to a sample possibly containing PSA, to obtain the sialidase-treated sample;
   (b) bringing into contact a lectin having an affinity for a β-N-acetylgalactosamine residue with the sialidase-treated sample, to separate into a bound fraction PSA having a β-N-acetylgalactosamine residue from a nonbound fraction of PSA lacking a β-N-acetylgalactosamine residue;
   (c) determining an amount of PSA having a β-N-acetylgalactosamine residue in the sialidase-treated sample of the bound fraction by an immunoassay using an antibody specific to PSA and a lectin having an affinity for β-N-acetylgalactosamine residue, or antibodies specific to PSA.

3. The method for determining an amount, if any, of PSA having a β-N-acetylgalactosamine residue and/or a sialic acid α(2,6) β-N-acetylgalactosamine residue according to claim 2, wherein the amount of PSA having β-N-acetylgalactosamine residue and a sialic acid α(2,6) β-N-acetylgalactosamine residue is determined
   (1) by measuring an amount of separated PSA having β-N-acetylgalactosamine residue in the bound fraction using an antibody specific to PSA and a lectin having an affinity for β-N-acetylgalactosamine residue, or antibodies specific to PSA,
   (2) by measuring an amount of PSA in a sample before the separation using antibodies specific to PSA, and measuring an amount of the separated PSA having β-N-acetylgalactosamine residue in the bound fraction using an antibody specific to PSA and a lectin having an affinity for β-N-acetylgalactosamine residue or antibodies specific to PSA, or
   (3) by measuring an amount of PSA in a sample before the separation using antibodies specific to PSA, and measuring an amount of the separated PSA lacking β-N-acetylgalactosamine residue in the nonbound fraction using antibodies specific to PSA.

4. The method for determining an amount, if any, of PSA having a β-N-acetylgalactosamine residue and/or a sialic acid α(2,6) β-N-acetylgalactosamine residue according to claim 3, wherein the amount of PSA having β-N-acetylgalactosamine residue is determined by measuring total PSA or free PSA.

5. The method for determining an amount, if any, of PSA having a β-N-acetylgalactosamine residue and/or a sialic acid α(2,6) β-N-acetylgalactosamine residue according to claim 1, wherein the lectin is *Trichosanthes japonica* agglutinin-II or *Wisteria floribunda* agglutinin.

6. The method for determining an amount, if any, of PSA having a β-N-acetylgalactosamine residue and/or a sialic acid α(2,6) β-N-acetylgalactosamine residue according to claim 1, wherein the lectin further has an affinity for fucose α(1,2) galactose residue.

7. The method for determining an amount, if any, of PSA having a β-N-acetylgalactosamine residue and/or a sialic acid α(2,6) β-N-acetylgalactosamine residue according to claim 1, wherein the sample is obtained from a patient suspected of having prostate cancer.

* * * * *

SEQUENCE LISTING

```
<160> NUMBER OF SEQ ID NOS: 18

<210> SEQ ID NO 1
<211> LENGTH: 4246
<212> TYPE: DNA
<213> ORGANISM: Homo sapiens

<400> SEQUENCE: 1
gaaagtccct gactggagtt ggcagccaag ccaggccctg gagtgggcac ccagagggaa      60
gacaggttgg ctaatttcct ggagcccta agggtgcaag ggggaagaac acccacccgc     120
aaagccccgt agggctggac cctacgttag cctgccctgc tcggggttgg cgatgctgga     180
ggtgggcctt ggaccagaga aaatgcttta attaggtgac aagcgggcag aggcctttgt     240
ctctggcgcc ggcagccacg gccccgctg acggcgtggg aaacagaccc tgttccactc     300
cggtctccag ccttggaatg gttgccttcg tgcagtgcag gaggacgcgg cagagggcgg     360
acgatcgctc cactcgccgg gaccaggtgc gggggccctg cccagccgct ggggcgtggc     420
caggctcgaa gcacccaggt gtcggggcc gactctaagc cctggcaccg gaagagagag     480
ggcggcggat tggacctccc ggctccagca ttgcaactgg gcgctccgtc tcctggtcca     540
cgcaatgatg ctgcggctgc tcagaagcca ggtagcctgc cctgggtgaa gccttcgcgc     600
aggtcaatga cggggcggag gggcagggcg cggtcccctg catcccgat ctggggagcg     660 gtgggcccag gggccatcgc cttagcccct ggcgctgggg ctcggcgcca agtgacgggc     720
ggggctccac cttccagcca tccgcccggc ccgggagggc ggacgctgcg agactcccgg     780
ccgcgccctc tccttcctct cctccccaag ccctcgctgc cagtccggac aggctgcgcg     840
gaggggaggg ctgccgggcc ggatagccgg acgcctggcg ttccaggggc ggccggatgt     900
ggcctgcctt tgcggagggt gcgctccggc cacgaaaagc ggactgtgga tctgccacct     960
gcaagcagct cggccatgtg gctccggagc catcgtcagc tctgcctggc cttcctgcta    1020
gtctgtgtcc tctctgtaat cttcttcctc catatccatc aagacagctt tccacatggc    1080
```

```
ctaggcctgt cgatcctgtg tccagaccgc cgcctggtga caccccagt ggccatcttc    1140 tgcctgccgg gtactgcgat gggccccaac gcctcctctt cctgtccca gcaccctgct    1200 tccctctccg gcacctggac tgtctacccc aatggccggt ttggtaatca gatgggacag   1260
tatgccacgc tgctggctct ggcccagctc aacggccgcc gggcctttat cctgcctgcc   1320
atgcatgccg ccctggcccc ggtattccgc atcaccctgc ccgtgctggc cccagaagtg   1380
gacagccgca cgccgtggcg ggagctgcag cttcacgact ggatgtcgga ggagtacgcg   1440
gacttgagag atcctttcct gaagctctct ggcttcccct gctcttggac tttcttccac   1500
catctccggg aacagatccg cagagagttc accctgcacg accaccttcg ggaagaggcg   1560
cagagtgtgc tgggtcagct ccgcctgggc cgcacagggg accgcccgcg cacctttgtc   1620
ggcgtccacg tgcgccgtgg ggactatctg caggttatgc ctcagcgctg aagggtgtg   1680 gtgggcgaca gcgcctacct ccggcaggcc atggactggt ccgggcacg gcacgaagcc    1740 cccgttttcg tggtcaccag caacggcatg gagtggtgta agaaaaacat cgacacctcc   1800
cagggcgatg tgacgtttgc tggcgatgga caggaggcta ccgtggaa agactttgcc    1860 ctgctcacac agtgcaacca caccattatg accattggca ccttcggctt ctgggctgcc   1920
tacctggctg gcggagacac tgtctacctg gccaacttca ccctgccaga ctctgagttc   1980
ctgaagatct ttaagccgga ggcggccttc ctgcccgagt gggtgggcat taatgcagac   2040
ttgtctccac tctggacatt ggctaagcct tgagagccag ggagactttc tgaagtagcc   2100
tgatctttct agagccagca gtacgtggct tcagaggcct ggcatcttct ggagaagctt   2160
gtggtgttcc tgaagcaaat gggtgcccgt atccagagtg attctagttg ggagagttgg   2220
agagaagggg gacgtttctg gaactgtctg aatattctag aactagcaaa acatctttc    2280 ctgatggctg gcaggcagtt ctagaagcca cagtgcccac ctgctcttcc cagcccatat   2340
ctacagtact tccagatggc tgcccccagg aatggggaac tctccctctg gtctactcta   2400
gaagaggggt tacttctccc ctgggtcctc caaagactga aggagcatat gattgctcca   2460
gagcaagcat tcaccaagtc cccttctgtg tttctggagt gattctagag ggagacttgt   2520
tctagagagg accaggttg atgcctgtga agaaccctgc agggccctta tggacaggat    2580
ggggttctgg aaatccagat aactaaggtg aagaatcttt ttagtttttt tttttttttt    2640
ttggagacag ggtctcgctc tgttgcccag gctggagtgc agtggcgtga tcttggctca   2700
ctgcaacttc cgcctcctgt gttcaagcga ttctcctgtc tcagcctcct gagtagatgg   2760
gactacaggc acaggccatt atgcctggct aatttttgta tttttagtag agacagggtt    2820
tcaccatgtt ggccaggatg gtctcgatct cctgaccttg tcatccacct gtcttggcct   2880
cccaaagtgc tgggattact ggcatgagcc actgtgccca gccggatat ttttttttta    2940 attatttatt tatttattta tttattgaga cggagtcttg ctctgtagcc caggccagag   3000
tgcagtggcg cgatctcagc tcactgcaag ctctgcctcc cgggttcatg ccattctgcc   3060
tcagcctcct gagtagctgg gactacaggc gcccgccacc acgcccggct aattttttt    3120 gtatttttag tagagacggg gtttcatcgt gttaaccagg atggtctcga tctcctgacc   3180
tcgtgatctg cccacctcgg cctcccacag tgctgggatt accggcgtga ccaccatgc    3240 ctggcccgga taatttttt taatttttgt agagacgagg tcttgtgata ttgcccaggc    3300
tgttcttcaa ctcctgggct caagcagtcc tcccaccttg gcctcccaga atgctgggtt   3360
tatagatgtg agccagcaca ccgggccaag tgaagaatct aatgaatgtg caacctaatt   3420
```

```
gtagcatcta atgaatgttc caccattgct ggaaaaattg agatggaaaa caaaccatct    3480
ctagttggcc agcgtcttgc tctgttcaca gtctctggaa aagctggggt agttggtgag    3540
cagagcggga ctctgtccaa caagccccac agcccctcaa agacttttt ttgtttgttt     3600 tgagcagaca ggctaaaatg tgaacgtggg gtgagggatc actgccaaaa tggtacagct    3660
tctggagcag aactttccag ggatccaggg acactttttt ttaaagctca taaactgcca    3720
agagctccat atattgggtg tgagttcagg ttgcctctca caatgaagga agttggtctt    3780
tgtctgcagg tgggctgctg agggtctggg atctgttttc tggaagtgtg caggtataaa    3840
cacaccctct gtgcttgtga caaactggca ggtaccgtgc tcattgctaa ccactgtctg    3900
tccctgaact cccagaacca ctacatctgg ctttgggcag gtctgagata aaacgatcta    3960
aaggtaggca gacctggac ccagcctcag atccaggcag gagcacgagg tctggccaag     4020
gtggacgggg ttgtcgagat ctcaggagcc ccttgctgtt ttttggaggg tgaaagaaga    4080
aaccttaaac atagtcagct ctgatcacat cccctgtcta ctcatccaga ccccatgcct    4140
gtaggcttat cagggagtta cagttacaat tgttacagta ctgttcccaa ctcagctgcc    4200
acgggtgaga gagcaggagg tatgaattaa aagtctacag cactaa                   4246

<210> SEQ ID NO 2
<211> LENGTH: 3463
<212> TYPE: DNA
<213> ORGANISM: Homo sapiens

<400> SEQUENCE: 2
gcggccgcga tgccgcggct cccggtgaag aagatccgta agcagatgaa gctgctgctg      60
ctgctgctgc tgctgagctg cgccgcgtgg ctcacctacg tgcacctggg cctggtgcgc     120
cagggacgcg cgctgcgcca cgcgcctggg c tacgggcgag atggtgagaa gctgaccagt    180
gagaccgacg gccgggggt ccacgctgcg ccatccacac agagggctga ggactccagt      240
gagagccgtg aagaggagca agcgcccgaa ggtcgggacc tagacatgct gtttcctggg     300
ggggctggga ggctgccact gaacttcacc catcagacac ccccatggcg ggaggagtac     360
aaggggcagg tgaacctgca cgtgtttgag gactggtgtg gggcgccgt gggccacctg      420 aggaggaacc tgcacttccc gctgttccct catacgcgca ccaccgtgaa gaagttggcc     480
gtgtccccca gtggaagaa ctatggactc cgtatttttg gtttcatcca cccggcgagg      540
gacggagacg tccagttttc tgtggcctca gacgacaact cggagttctg gctgagtctg     600
gacgagagcc ctgctgctgc ccagcttgtg gcctttgtgg gcaagactgg ctccgagtgg    660
acagcgcctg gagaattcac caagttcagc tcccaggtgt ccaagcccag gcggctcatg    720
gcctcccgga ggtactactt tgagttgctg cacaagcagg acgaccgcgg ctcggaccac    780
gtggaagtgg gctggcgagc tttcctgccc ggcctgaagt tcgaggtcat cagctctgct    840
cacatctccc tgtacacaga tgagtcagcc ttgaagatgg accacgtggc gcacgtcccc    900
cagtctccag ccagccacgt ggggggggcgt ccgccgcagg aggaaccag cgcagacatg    960 ctgcggccag atcccaggga tacctttttc ctcactccac gcatggaatc ttcgagcctg   1020
gagaacgtgc tggagccctg cgcctacgcc cccacctacg tggtcaagga cttcccgatc   1080
gccagatacc agggcctgca atttgtgtac ctgtccttcg tttatcccaa cgactacact   1140
cgcctcaccc acatggagac ggacaacaag tgcttctacc gcgagtctcc gctgtatctg   1200
gagagggttg gttctctata atacatgaag atggacaagg aggagggga tgaggatgaa    1260 gaagacgagg tgcagcgccg agccttcctc ttcctcaacc cggacgactt cctggacgac   1320
```

```
gaggacgagg gggagctgct cgacagcctg agcccaccg aggcggcccc gcccaggagc    1380
ggcccccagt cccccgcccc agcagccccc gcccagcccg agccacccct cgccccgccg    1440 accccctcccc gccccggga cgggggacc cccaggcact cccgggccct gagctgggcc    1500
gccagggccg cccgcccttt gccgctcttc ttgggccgag ctccgccccc gcgccctgca    1560
gtggagcagc cgcccccaaa ggtgtacgtg accagggtgc ggccgggaca gcgggcatcc    1620
ccccgggccc cagcgccgcg tgcgcccctgg ccgcccttcc ctggcgtctt cctgcacccc    1680
aggcctctgc ccagagtgca gctgcgggcg ccccacgcc caccccggcc cacggccgc    1740 aggaccggcg gcccccaggc cacacagccg aggcccccag cccgggcgca ggccacccaa    1800
gggggccggg agggccaggc gcgcacgctg ggacctgcgg cgcccacagt ggactcaaac    1860
ttgtcctccg aagcgcggcc cgtgacctcc ttcctgagct tgtcccaggt gtccgggccg    1920
cagctgcccg ggagggcga agaggaggag aaggggagg acgatggggc cccgggcgac    1980
gaggccgcgt cggaggacag cgaggaggcc gcgggcccgg cgctcggacg ctggcgtgag    2040
gacgccatcg actggcagcg cacgttcagc gtgggcgccg tggacttcga gctgctgcgc    2100
tcggactgga acgacctgcg atgcaacgtt tcggggaacc tgcagctgcc ggaggcggag    2160
gccgtggacg tgaccgctca gtacatggag cggctgaacg cgcgccacgg cgggcgcttc    2220
gcgcttctgc gcatcgtgaa cgtggagaag cgccgggact cggcgcgagg gagtcgcttc    2280
ctgctggagc tggagctgca ggagcgcggg ggcggccgcc tgcgactgtc cgagtacgtc    2340
ttcctgcggc tgccgggagc ccgcgtaggg gatgcagacg gagaaagtcc cgaacccgct    2400
cccgccgcct ccgtgcgccc cgacggccgc cccgagctct gccggccact gcgcctggcc    2460
tggcgccagg acgtgatggt tcacttcatc gtgccagtga aaaccaggc acggtgggtg    2520 gcacagttcc tggcggacat ggctgcgctg cacgcgcgca ccggggactc gcgtttcagc    2580
gtcgtcctgg tggatttcga gagcgaggat atggacgtgg agcgggccct gcgcgccgcg    2640
cgcctgcccc ggtaccagta cctgagacga accgggaact tcgagcgctc cgccgggctg    2700
caggcgggag tggacgcggt agaggacgcc agcagcatcg tgttcctctg cgacctgcac    2760
atccacttcc cacccaacat cctggacggc atccgcaagc actgcgtgga gggcaggctg    2820
gccttcgcgc ccgtggtcat cgcgcctgagc tgcgggagct cgccccggga ccccacggt    2880 tactgggagg tgaacggctt tggcctttt gggatctaca gtcggactt tgaccgggtt    2940 ggaggaatga acacggagga gttccgagac cagtgggggg gtgaagactg ggagctcctg    3000
gacagggtcc tgcaggcagg gctggagtg gagcggctcc gactgcggaa tttctatcac    3060
cactaccact ccaagagggg catgtggagc gtccgcagca ggaagggctc tcgcacgggg    3120
gcgtcttgag gacgggcagc ccctcccagc cccgtggga gtcccgaggc agctgctggg    3180
ggctgggctt tgagctcggt cccgagagac ccggcagggc tggtcagagg ggcacagcca    3240
ccgcctgtgc ctgcccctct ctggcccact gggcgtcgtg cccctccccg agaggcagc    3300 cttcacggcg ggtcagggcc tggccttggt ccccactctg cgatgatttc tgtgaaattt    3360
tgctgtagcg atgacattgt tttcagaatt tccaagagtt ctgtctgttc tgttttttat    3420
tcagaatgaa atgaaatatt ttttttagtt ctgaaaaaa aaa                      3463
```

<210> SEQ ID NO 3
<211> LENGTH: 19
<212> TYPE: DNA
<213> ORGANISM: Artificial
<220> FEATURE:

<223> OTHER INFORMATION: FUT1 F primer

<400> SEQUENCE: 3
aacgcctcct cttcctgtc                                                  19

<210> SEQ ID NO 4
<211> LENGTH: 20
<212> TYPE: DNA
<213> ORGANISM: Artificial
<220> FEATURE:
<223> OTHER INFORMATION: FUT1 R primer

<400> SEQUENCE: 4
tggggtagac agtccaggtg                                                 20

<210> SEQ ID NO 5
<211> LENGTH: 20
<212> TYPE: DNA
<213> ORGANISM: Artificial
<220> FEATURE:
<223> OTHER INFORMATION: FUT2 F primer

<400> SEQUENCE: 5
cctcaacatc aaaggcactg                                                 20

<210> SEQ ID NO 6
<211> LENGTH: 20
<212> TYPE: DNA
<213> ORGANISM: Artificial
<220> FEATURE:
<223> OTHER INFORMATION: FUT2 R primer

<400> SEQUENCE: 6
ggcctattgc attgatcgtc                                                 20

<210> SEQ ID NO 7
<211> LENGTH: 20
<212> TYPE: DNA
<213> ORGANISM: Artificial
<220> FEATURE:
<223> OTHER INFORMATION: B4GALNT2 F primer

<400> SEQUENCE: 7
gatttttcca accctggat                                                  20

<210> SEQ ID NO 8
<211> LENGTH: 19
<212> TYPE: DNA
<213> ORGANISM: Artificial
<220> FEATURE:
<223> OTHER INFORMATION: B4GALNT2 R primer

<400> SEQUENCE: 8
gaagttgacc acgccactg                                                  19

<210> SEQ ID NO 9
<211> LENGTH: 20
<212> TYPE: DNA
<213> ORGANISM: Artificial
<220> FEATURE:
<223> OTHER INFORMATION: B4GANT3 F primer

<400> SEQUENCE: 9
aggtcacgcg agtcttcttg                                                 20

```
<210> SEQ ID NO 10
<211> LENGTH: 20
<212> TYPE: DNA
<213> ORGANISM: Artificial
<220> FEATURE:
<223> OTHER INFORMATION: B4GANT3 R primer

<400> SEQUENCE: 10
acaatgcgct gtagctggta                                               20

<210> SEQ ID NO 11
<211> LENGTH: 18
<212> TYPE: DNA
<213> ORGANISM: Artificial
<220> FEATURE:
<223> OTHER INFORMATION: B4GANT4 F primer

<400> SEQUENCE: 11
actgggagct cctggaca                                                 18

<210> SEQ ID NO 12
<211> LENGTH: 21
<212> TYPE: DNA
<213> ORGANISM: Artificial
<220> FEATURE:
<223> OTHER INFORMATION: B4GALNT4 R primer

<400> SEQUENCE: 12
tggtgataga aattccgcag t                                             21

<210> SEQ ID NO 13
<211> LENGTH: 20
<212> TYPE: DNA
<213> ORGANISM: Artificial
<220> FEATURE:
<223> OTHER INFORMATION: ST6GAL1 F primer

<400> SEQUENCE: 13
tcagcgggat ctctgaagtc                                               20

<210> SEQ ID NO 14
<211> LENGTH: 19
<212> TYPE: DNA
<213> ORGANISM: Artificial
<220> FEATURE:
<223> OTHER INFORMATION: ST6GAL1 R primer

<400> SEQUENCE: 14
aaacctcagg actgcgtca                                                19

<210> SEQ ID NO 15
<211> LENGTH: 19
<212> TYPE: DNA
<213> ORGANISM: Artificial
<220> FEATURE:
<223> OTHER INFORMATION: ST6GAL2 F primer

<400> SEQUENCE: 15
tccttgggcg aggaaatag                                                19

<210> SEQ ID NO 16
<211> LENGTH: 23
<212> TYPE: DNA
<213> ORGANISM: Artificial
<220> FEATURE:
<223> OTHER INFORMATION: ST6GAL2 R primer
```

```
<400> SEQUENCE: 16
cccaacatct ttctcataac cac                                         23

<210> SEQ ID NO 17
<211> LENGTH: 19
<212> TYPE: DNA
<213> ORGANISM: Artificial
<220> FEATURE:
<223> OTHER INFORMATION: GAPDH F primer

<400> SEQUENCE: 17
atccacatcg ctcagacac                                              19

<210> SEQ ID NO 18
<211> LENGTH: 19
<212> TYPE: DNA
<213> ORGANISM: Artificial
<220> FEATURE:
<223> OTHER INFORMATION: GAPDH R primer

<400> SEQUENCE: 18
gcccaatacg accaaatcc                                              19
```